(12) United States Patent
Zhang et al.

(10) Patent No.: US 10,471,076 B2
(45) Date of Patent: Nov. 12, 2019

(54) COMPOSITIONS AND METHODS TO TREAT VISION DISORDERS

(71) Applicants: YouHealth Biotech, Limited, Grand Cayman OT (KY); The Regents of the University of California, Oakland, CA (US)

(72) Inventors: Kang Zhang, San Diego, CA (US); Rui Hou, Shenyang (CN); Huimin Cai, Shenyang (CN)

(73) Assignees: YOUHEALTH BIOTECH, LIMITED, Grand Cayman (KY); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/139,192

(22) Filed: Apr. 26, 2016

(65) Prior Publication Data

US 2017/0065617 A1    Mar. 9, 2017

Related U.S. Application Data

(63) Continuation of application No. PCT/US2015/046453, filed on Aug. 24, 2015.

(60) Provisional application No. 62/194,120, filed on Jul. 17, 2015, provisional application No. 62/040,721, filed on Aug. 22, 2014.

(51) Int. Cl.
*A61K 31/575* (2006.01)
*A61K 47/40* (2006.01)
*A61K 9/00* (2006.01)
*A61K 31/573* (2006.01)

(52) U.S. Cl.
CPC .......... *A61K 31/575* (2013.01); *A61K 9/0014* (2013.01); *A61K 9/0048* (2013.01); *A61K 31/573* (2013.01); *A61K 47/40* (2013.01)

(58) Field of Classification Search
CPC .... A61K 31/575; A61K 47/40; A61K 9/0014; A61K 9/0048
See application file for complete search history.

(56) References Cited

U.S. PATENT DOCUMENTS

2006/0121024 A1   6/2006  Javitt
2008/0318843 A1  12/2008  Schultz et al.
2010/0068251 A1   3/2010  Ali et al.
2011/0136773 A1   6/2011  Pianowski et al.

FOREIGN PATENT DOCUMENTS

WO    WO-2006059357 A2   6/2006
WO    WO-2014015024 A2   1/2014
WO    WO-2014035451 A1   3/2014
WO    WO-2016029199 A1   2/2016

OTHER PUBLICATIONS

Abagyan et al. Optimal protocol and trajectory visualization for conformational searches of peptides and proteins. J Mol Biol 225:519-532 (1992).
Adzhubei et al. A method and server for predicting damaging missense mutations. Nature Methods 7:248-249 (2010).
Bligh et al. A rapid method of total lipid extraction and purification. Can J Biochem Physiol.37(8):911-917 (1959).
Bloch. The biological synthesis of cholesterol. Science 150:19-28 (1965).
Bloemendal et al. Ageing and vision: structure, stability and function of lens crystallins. Prog Biophys Mol Biol 86(3):407-485 (2004).
Bradford. A rapid and sensitive method for the quantitation of microgram quantities of protein utilizing the principle of protein-dye binding. Anal Biochem 72:248-254 (1976).
Braun et al. Multiple molecular architectures of the eye lens chaperone αBcrystallin elucidated by a triple hybrid approach. PNAS 108:20491-20496 (2011).
Cardozo et al. Homology modeling by the ICM method. Proteins 23:403-414 (1995).
Cenedella et al. Direct perturbation of lens membrane structure may contribute to cataracts caused by U18666A, an oxidosqualene cyclase inhibitor. J Lipid Res 45:1232-1241 (2004).
Depristo et al. A framework for variation discovery and genotyping using next-generation DNA sequencing data. Nature Genet 43:491-498 (2011).
Diehn et al. Differential gene expression in anatomical compartments of the human eye. Genome Biol 6:R74 (2005).
Dobson. Protein folding and misfolding. Nature 426:884-890 (2003).
Ecroyd et al. Crystallin proteins and amyloid fibrils. Cell Mol Life Sci 66:62-81 (2009).
Garty et al. Sustained antibiotic release from an intraocular lens-hydrogel assembly for cataract surgery. Invest Ophthalmol Vis Sci 52(9):6109-6116 (2011).
Geraldine et al. Prevention of selenite-induced cataractogenesis by acetyl-L-carnitine: an experimental study. Exp Eye Res 83:1340-1349 (2006).
Gu et al. A novel mutation in AlphaA-crystallin (CRYAA) caused autosomal dominant congenital cataract in a large Chinese family. Hum Mutat 29:769 (2008).
Gwon et al. Ophthalmic rods. New ocular drug delivery devices. Ophthalmology 93(9 Suppl):82-85 (1986).

(Continued)

*Primary Examiner* — Zohreh A Fay
(74) *Attorney, Agent, or Firm* — Wilson Sonsini Goodrich & Rosati

(57) ABSTRACT

The present invention provides sterols and uses thereof to treat vision disorders. In one embodiment, composition comprising pharmaceutically effective amount of lanosterol is used to treat and/or prevent vision disorders in a subject. In another embodiment, composition comprising pharmaceutically effective amount of lanosterol is used to treat cataract or blindness/impaired vision in a subject. In yet another embodiment, composition comprising lanosterol is used to dissolve amyloid-like fibrils of crystallin proteins.

16 Claims, 19 Drawing Sheets

(56) References Cited

OTHER PUBLICATIONS

Huff et al. Lord of the rings—the mechanism for oxidosqualene: lanosterol cyclase becomes crystal clear. Trends Pharmacol Sci 26:335-340 (2005).
La Croix. Cataracts: When to refer. Top Companion Anim Med 23:46-50 (2008).
Li et al. A novel mutation impairing the tertiary structure and stability of γC-crystallin (CRYGC) leads to cataract formation in humans and zebrafish lens. Hum Mutat 33:391-401 (2012).
Li et al. Fast and accurate long-read alignment with Burrows-Wheeler transform. Bioinformatics 26:589-595 (2010).
Makri et al. Saffron administration prevents selenite-induced cataractogenesis. Mol Vis 19:1188-1197 (2013).
Meehan et al. Amyloid fibril formation by lens crystallin proteins and its implications for cataract formation. J Biol Chem 279(5):3413-3419 (2004).
Moreau et al. Protein misfolding and aggregation in cataract disease and prospects for prevention. Trends Mol Med 18:273-282 (2012).
Mori et al. Lanosterol synthase mutations cause cholesterol deficiency-associated cataracts in the Shumiya cataract rat. J Clin Invest 116:395-404 (2006).
Nagineni et al. Human fetal lens epithelial cells in culture: an in vitro model for the study of crystallin expression and lens differentiation. Curr Eye Res 8:285-291 (1989).
Ng et al. Predicting Deleterious Amino Acid Substitutions. Genome Research 11:863-874 (2001).
Pascolini et al. Global estimates of visual impairment: 2010. Br J Ophthalmol 96:614-618 (2012).
PCT/US2015/046453 International Search Report and Written Opinion dated Nov. 25, 2015.
Petrash. Aging and age-related diseases of the ocular lens and vitreous body. Invest Ophthalmol Vis Sci 54:ORSF54-ORSF59(2013).
Pollard et al. Detection of nonneutral substitution rates on mammalian phylogenies. Genome Res 20(1):110-121 (2010).
Ruf et al. The monotopic membrane protein human oxidosqualene cyclase is active as monomer. Biochem Biophys Res Commun 315:247-254 (2004).
Schwarz et al. MutationTaster2: mutation prediction for the deep-sequencing age. Nature Methods 11:361-362 (2014).
Seelow et al. HomozygosityMapper—an interactive approach to homozygosity mapping. Nucleic Acids Res. 37:W593-W599 (2009).
Sun et al. Conformational and functional differences between recombinant human lens αA- and αB-crystallin. J Biol Chem 272:6220-6225 (1997).
Thoma et al. Insight into steroid scaffold formation from the structure of human oxidosqualene cyclase. Nature 432:118-122 (2004).
Wagh et al. Polymers used in ocular dosage form and drug delivery systems. Asian J Pharm. 2(1):12-17 (2008).
Wang et al. A novel CRYGD mutation (p.Trp43Arg) causing autosomal dominant congenital cataract in a Chinese family. Hum Mutat 32:E1939-E1947 (2011).
Wang et al. The benefits of being β-crystallin heteromers: βB1-crystallin protects βA3-crystallin against aggregation during co-refolding. Biochemistry 50:10451-10461 (2011).
Xu et al. The congenital cataract-linked A2V mutation impairs tetramer formation and promotes aggregation of βB2-crystallin. PLoS One 7:e51200 (2012).
Zhang et al. Self-assembled lipid-polymer hybrid nanoparticles: a robust drug delivery platform. ACS Nano 2:1696-1702 (2008).
Zhao et al. Lanosterol reverses protein aggregation in cataracts. Nature 523(7562):607-611 (2015).
PCT/US2015/046453 International Preliminary Report on Patentability dated Mar. 9, 2017.
Cenedella. Cholesterol and Cataracts. Surv Ophthalmol 40(4):320-337 (1996).
Weeks et al. Effectiveness of Novel Chemical Inhibitors of *Staphylococcus aureus* Alpha-toxin In Vitro and In Vivo. IOVS Retrieved from the Internet: URL:http://iovs.arvojournals.org/article.a spx? articleid=2358262 (2 pgs) (2011).

Fig.2A
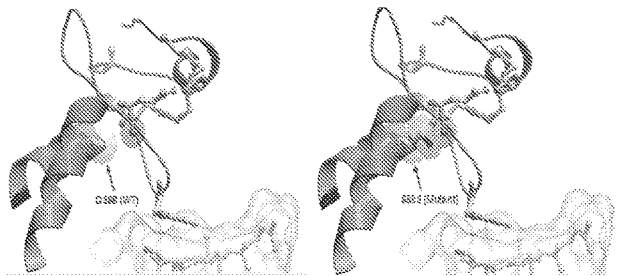
Fig.2B
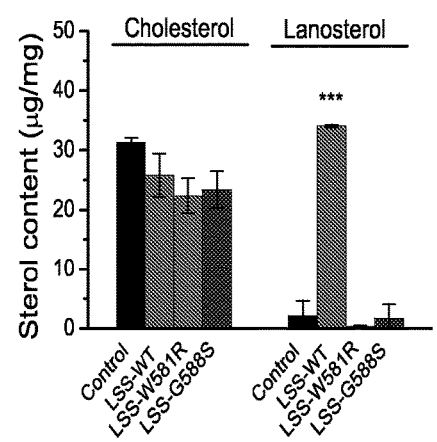
Fig.2C

COMPOSITIONS AND METHODS TO TREAT VISION DISORDERS

CROSS REFERENCE TO RELATED APPLICATIONS

This application is a continuation of International Application No. PCT/US2015/046453, filed Aug. 24, 2015, which claims the benefit of priority of U.S. Provisional Application No. 62/040,721, filed Aug. 22, 2014 and U.S. Provisional Application No. 62/194,120, filed Jul. 17, 2015, the content of which are hereby incorporated herein by reference in their entirety.

FIELD OF THE INVENTION

The disclosure generally relates to sterols and uses thereof to treat vision disorders that affect the normal function of the lens in the eye in a subject having or at risk of developing such vision disorders.

SUMMARY OF THE INVENTION

The invention provides a method of treating or preventing vision disorders, the method comprising administering to an individual in need thereof an effective amount of a lanosterol; and a prodrug or pharmaceutically acceptable salt thereof.

The invention also provides an ophthalmic pharmaceutical composition comprising a pharmaceutically acceptable ophthalmic carrier and lanosterol with a structure of formula I:

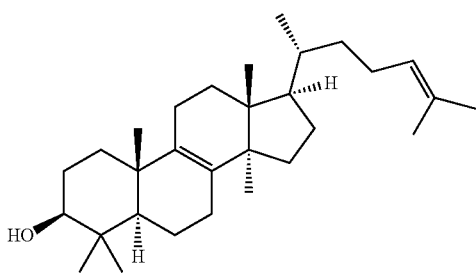

and a prodrug or pharmaceutically acceptable salt thereof.

In various aspects of the method, the vision disorder is a disorder of the eye that affects function, clarity and/or structure of the lens of the eye. Such eye diseases include, but are not limited to, cataracts of the eye, presbyopia of the eye, and nuclear sclerosis of the eye lens. In addition, vision disorders refer to retinal degeneration, such as Refsum disease, Smith-Lemli-Opitz syndrome (SLOS) and Schnyder crystalline corneal dystrophy (SCCD), abetalipoproteinemia and familial hypobetalipoproteinemia.

In one embodiment, the present invention provides a method of ameliorating at least one symptom associated with a vision disorder by administering to a subject a therapeutically or prophylactically effective amount of a sterol of formula 1. In various aspects of the method, the composition is administered topically, subconjunctivally, retrobulbarly, periocularly, subretinally, suprachoroidally, or intraocularly. Subjects that receive the invention sterol can include, but are not limited to mammals, avians, amphibians, reptiles and other vertebrates. In one embodiment, the subjects are horses, pigs, dogs, cats, rodents and/or other companion pets. In another embodiment, the subjects are humans.

In one embodiment, the present invention relate to an ophthalmic pharmaceutical composition comprising the invention sterol in an ophthalmic pharmaceutically acceptable carrier. In some embodiments, the pharmaceutical composition comprises lanosterol, or derivatives thereof in an ophthalmic pharmaceutically acceptable carrier. In certain embodiments of the invention, the pharmaceutically acceptable carrier is water, a buffer or a solution of sodium chloride. In some embodiments, the pharmaceutically acceptable carrier is sterile. In other embodiments, the pharmaceutically carrier is an ointment. In still other embodiments, the pharmaceutically acceptable carrier is a gel. Gels can be formulated using gel formulating materials that are well known in the art, including but not limited to, high viscosity carboxymethylcellulose, hydroxypropylmethylcellulose, polyethylene oxide and carbomer. In some aspects of the composition, the pharmaceutically acceptable ophthalmic carrier is a cyclodextrin. In one embodiment, the cyclodextrin is (2-hydroxypropyl)-β-cyclodextrin.

Certain embodiments of the invention also contemplate kits that comprise components useful for treating and/or preventing a symptom associated with a vision disorder. Such kits comprise a container comprising invention sterol in a pharmaceutically acceptable carrier and instructions for administering the invention sterol such that at least one symptom associated with the vision disorder is ameliorated or prevented. Such vision disorder includes, but is not limited to, cataracts, presbyopia, and nuclear sclerosis of the eye lens. In addition, vision disorders refer to retinal degeneration, such as Refsum disease, Smith-Lemli-Opitz syndrome (SLOS) and Schnyder crystalline corneal dystrophy (SCCD), abetalipoproteinemia and familial hypobetalipoproteinemia. The containers included in some of the kits contemplated herein are droppers for the administration of eye drops. In other embodiments, the container is a tube for dispensing ointment or gel. In still other embodiments, the container is any appropriate container for drug delivery including, but not limited to, a syringe, or other container appropriate for delivery of a drug ophthalmically or topical application.

In other aspects, the invention provides a method for inhibiting or preventing protein aggregation. In various aspects of the method, the protein is an amyloid-forming protein or a protein underlying a loss-of-function disease. In some aspects, the amyloid-forming protein is selected from the group consisting of Hsp27, αA-crystallin, αB-crystallin, βB2-crystallin, βB1-crystallin, γD-crystallin, Hsp22, Hsp20, tau, Alpha-synuclein, IAPP, beta-amyloid, PrP, Huntingtin, Calcitonin, Atrial natriuretic factor, Apolipoprotein AI, Serum amyloid A, Medin, Prolactin, Transthyretin, Lysozyme, Beta 2 microglobulin, Gelsolin, Keratoepithelin, Cystatin, Immunoglobulin light chain AL, and S-IBM. In other aspects, the protein underlying a loss-of-function disease is selected from the group consisting of mutant β-glucosidase, cystic fibrosis transmembrane receptor, hexosaminidase A, hexosaminidase B, β-galactosidase, and alpha-glucosidase.

Other features and advantages of the present disclosure will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description. The entire document is intended to be related as a unified disclosure, and it should be understood that all combinations of features described herein are contemplated, even if the combination of features are not found together in the same sentence, or paragraph, or section of this document. In addition to the foregoing, the invention includes, as an additional aspect, all embodiments of the invention narrower in scope in any way than the variations specifically mentioned above. For example, if aspects of the invention are described as "comprising" a feature, embodiments also are contemplated "consisting of" or "consisting essentially of" the feature.

In one embodiment, this invention discloses the use of a composition for the preparation of medicament to treat and/or prevent vision disorders in a subject, said composition comprises a pharmaceutically acceptable ophthalmic carrier and a pharmaceutically effective amount of lanosterol. Said subject is having or at risk of developing a vision disorder that affects the normal structure of the lens in the eye. Said subject may be selected from the group consisting of amphibians, reptiles, avians, and mammals; wherein said mammal may be selected from the group consisting of rodents, cats, dogs, pigs, horses and humans. In another embodiment, said vision disorder is selected from the group consisting of cataract, congenital cataracts, cortical opacities, posterior subcapsular cataract, presbyopia nuclear sclerosis, retinal degenerative disorder, Refsum disease, Smith-Lemli-Opitz syndrome, Schnyder crystalline corneal dystrophy, drusen, age-related macular degeneration, and diabetic retinopathy, and lanosterol inhibits crystallin protein aggregation.

In yet another embodiment, this invention discloses the use of a composition for the preparation of medicament to treat cataract or blindness/impaired vision in a subject, said composition comprises a pharmaceutically acceptable ophthalmic carrier and a pharmaceutically effective amount of lanosterol, wherein said lanosterol dissolves lens crystallin protein aggregate(s) in the eye of said subject; wherein the lens crystallin protein is any of α-crystallin, β-crystallin or γ-crystallin. The above mentioned composition may be formulated as an ophthalmic solution, an ophthalmic ointment, an ophthalmic wash, an intraocular infusion solution, a wash for anterior chamber, an internal medicine, an injection, or preservative for extracted cornea.

In yet another embodiment, this invention discloses a method for dissolving amyloid-like fibrils of crystallin proteins, comprising the step of contacting the amyloid-like fibrils with lanosterol in a sufficient amount and duration so as to dissolve the amyloid-like fibrils of crystalline proteins, wherein the method may be performed in situ, in vitro or in vivo. The method may be performed on a subject selected from the group consisting of amphibians, reptiles, avians, and mammals; wherein said mammal may be selected from the group consisting of rodents, cats, dogs, pigs, horses and humans.

In another embodiment, this invention discloses a kit for treating and/or preventing vision disorders that affect the normal structure of the eye in a subject, comprising a formulation of a pharmaceutically effective amount of lanosterol, a pharmaceutically acceptable carrier and instructions for administering said formulation such that said administration treats and/or prevents said vision disorder. In yet another embodiment, this invention discloses an ophthalmic pharmaceutical composition for treating and/or preventing vision disorders in a subject, said composition comprises a pharmaceutically acceptable ophthalmic carrier and a pharmaceutically effective amount of lanosterol; wherein said composition may be formulated as an ophthalmic solution, an ophthalmic ointment, an ophthalmic wash, an intraocular infusion solution, a wash for anterior chamber, an internal medicine, an injection, or preservative for extracted cornea.

In another embodiment, this invention discloses a method for identifying and/or treating a subject at risk of developing cataract or blindness/impaired vision associated with formation of lens crystallin protein aggregate(s) in an eye, comprising: a) assaying for amount of lanosterol synthase activity in the subject; b) determining whether the amount of lanosterol synthase activity is less than that of a control population without cataract or blindness/impaired vision, wherein an amount of lanosterol synthase activity less than that of a control population is indicative of a higher risk of developing cataract or blindness/impaired vision associated with the formation of lens crystallin protein aggregate(s); and c) treating the subject with lanosterol in an effective amount and duration so as to prevent or reverse formation of lens crystallin protein aggregate(s) in an eye of the subject, thereby identifying and treating the subject at risk of developing cataract or blindness/impaired vision associated with formation of lens crystallin protein aggregate(s) in the eye of the subject.

In another embodiment, this invention discloses a method of identifying and/or treating a subject at risk of developing cataract or blindness/impaired vision associated with formation of lens crystallin protein aggregate(s) in an eye of the subject, comprising: a) determining whether both alleles of the lanosterol synthase gene are affected with a mutation which decreases lanosterol synthase expression or activity, wherein presence of a mutation in both alleles of the lanosterol synthase increases the risk of developing cataract or blindness/impaired vision associated with formation of lens crystallin protein aggregate(s) in an eye of a subject; and b) treating the subject with lanosterol in an effective amount and duration so as to prevent or reverse formation of lens crystallin protein aggregate(s) in an eye of the subject, thereby identifying and treating the subject at risk of developing cataract or blindness/impaired vision associated with formation of lens crystallin protein aggregate(s) in the eye or the subject. In one embodiment, the mutation in lanosterol synthase gene is at codon 581 changing tryptophan (W) to arginine (R) or codon 588 changing glycine (G) to serine (S).

BRIEF DESCRIPTION OF THE DRAWINGS

FIG. 1A, shows Pedigrees of affected families and cataract phenotype. Squares and circles indicate males and females respectively. 1, wild-type allele; W581R and G588S are the two mutations. FIG. 1B, Upper panel, shows DNA sequencing data of an unaffected individual and an affected child (II-1) with a homozygous W581R mutation; lower panel, shows DNA sequencing data of an unaffected individual and an affected child (IV-1) with a homozygous G588S mutation. The underlined sequence indicates the nucleic acid change. FIG. 1C, Left, shows colour photograph of patient 1's right eye in the first pedigree (IV-1) with a total cataract; right, shows colour photograph of patient 2's right eye in the same pedigree (IV-3) with a cataract.

FIG. 2A, FIG. 2B, and FIG. 2C show LSS mutations abolished the cyclase enzymatic function. FIG. 2A, shows Conservation of W581R and G588 in LSS across several species: *Homo sapiens, Pan troglodytes, Bos taurus, Mus musculus, Rattus norvegicus, Gallus gallus* and *Danio rerio*.

FIG. 2B, shows Computer modelling of LSS structure and impact of the LSS W581R and G588S mutations. A computer modelling analysis identifies a loop originating from C584 and ending at E578 with the key side chain of W581 at the tip of the loop stabilizing the sterol. The loop is fixed by an S-S bridge and the E578-R639 salt bridge. Amide nitrogen N of G588 interacts with the C584 from the previous helical turn and the Cα hydrogen of G588 is in close proximity to the critical E578, which then forms a strong salt bridge with R639 of the same supporting helix. The mutation G588S causes the side chain of the serine to clash into the E578 residue of the loop and is incompatible with the structure. Arrow indicates the location of the mutant side chain. FIG. 2C, shows Effect of engineered expression of the wild-type protein (WT LSS) and LSS mutants on sterol content. Wild-type LSS markedly increased lanosterol production, whereas neither W581R nor the G588S mutant exhibited any cyclase activity. n=3 in each group; ***$P<0.001$.

FIG. 3A, shows Confocal images of crystallin protein aggregates in human lens progenitor cells. The cataract-causing Y118D mutant of αA-crystallin formed p62-positive intracellular inclusion bodies or aggresomes. Green, eGFP-crystallin proteins; red, p62; blue, nuclei. Cells transfected with peGFP-N1 were used as a control. FIG. 3B shows Confocal images of inhibitory effect of LSS on crystalline aggregates. FIG. 3C, shows Inhibition of crystallin mutant aggregation by wild-type LSS (WT LSS) and lanosterol, but not mutant LSS or cholesterol. FIG. 3D, shows Increase in soluble αA-crystallin (Y118D) mutant protein by co-expression of wild-type LSS but not LSS mutants (Y118D co-expressed with pcDNA3.1-N-Flag was used as a control). Quantitative analysis was performed using densitometry of crystallin proteins by western blot analysis of the supernatant or insoluble fraction of cell lysates. n=3 in each group; representative western blot analysis is shown in—FIG. 9C; *$P<0.05$, **$P<0.01$. FIG. 3E, shows Confocal images of the re-dissolution of pre-formed crystalline aggregates by lanosterol. FIG. 3F, shows Lanosterol significantly reduced the intracellular aggregation by various cataract-causing mutant crystallin proteins in a concentration-dependent manner (n=3, $P<1\times10^{-4}$). Cholesterol did not reduce intracellular aggregation (n=3, $P>0.1$). FIG. 3G, shows Lanosterol increased the soluble fractions of various crystallin mutants in human lens progenitor cells. n=3; $P<0.001$. FIG. 3H, shows Effects of DMSO, cholesterol or lanosterol on αA-crystallin Y118D aggregates in human lens progenitor cells by serial live cell imaging. FIG. 3I, shows Effect of lanosterol on dissolution of intracellular crystallin aggregates over time (n=22 from 3 biological replicates). The mean±SD values are shown as black symbols. The data are best fitted by the single exponential decay process (red line).

FIG. 4A, shows Negatively stained TEM photographs of aggregates of αA-crystallin mutant proteins treated by a liposome vehicle, cholesterol or lanosterol in liposomes. Images in the right column of the lanosterol group show a 5× magnification of the image on their right. FIG. 4B, shows Effect of lanosterol on the re-dissolution of crystallin aggregates by ThT fluorescence (n=3). FIG. 4B, left, shows b/gamma-crystallin mutants; FIG. 4B, right, shows a-crystallin mutants. Each bar results from three independent samples.

FIG. 5A, shows Photographs of a cataractous rabbit lens treated with lanosterol showing increased lens clarity. FIG. 5A, left, before treatment; FIG. 5A, right, after treatment. FIG. 5B, shows Boxplot of the quantification of the treatment effect of lanosterol (n=13). FIG. 5C, shows Photographs of a cataractous dog lens treated with lanosterol showing increased lens clarity. FIG. 5C, left, shows before treatment; FIG. 5C, right, shows after treatment. FIG. 5D, shows, Boxplot of the quantification of the treatment effect of lanosterol (n=7). Range, median (horizontal line) and mean (circle) are presented. Crosses indicate the maximum and minimum cataract grades measured. Whiskers indicate the standard deviation and the box encompasses a 40% confidence interval.

FIG. 8A, shows R116C mutant of αA-crystallin. FIG. 8B, shows R120G mutant of αB-crystallin. FIG. 8C, shows V187E mutant of βB2-crystallin. FIG. 8D, shows G129C mutant of γC-crystallin. FIG. 8E, shows W43R mutant of γD-crystallin. Human lens progenitor cells were co-transfected with either the wild-type or the mutated Flag-LSS gene and the mutant GFP-crystallin gene for 4 h and cultured for 16 h in fresh culture medium. All crystallin mutants formed p62-positive aggregates as indicated by the co-localization of the mutant crystallins and p62. Cells co-transfected with GFP-crystallin and pcDNA3.1-N-Flag were used as controls. The formation of intracellular aggregates of various crystallin proteins was visualized by fluorescence of GFP (green). Wild-type or mutated LSS was detected with an anti-Flag antibody (red), p62 was stained using an anti-p62 antibody, while the nuclei were stained and visualized by Hoechst 33342 staining (blue). Quantitative analysis of cells with aggregates is summarized in FIG. 3C.

FIG. 9C, shows Human lens progenitor cells were co-transfected with wild-type or mutant LSS plus αA-crystallin (Y118D). αA-crystallin (Y118D) co-expressed with pcDNA3.1-N-Flag was used as a control. After transfection for 4 h and incubation in fresh culture medium for another 24 h, the cells were lysed and centrifuged to separate supernatant and insoluble fractions. LSS and crystallin fusion proteins were detected by antibodies against Flag and GFP, respectively. Red arrows indicate higher crystalline content in the soluble fraction versus in the insoluble fraction in cells containing the WT-LSS. Data were quantified from three independent experiments and summarized in FIG. 3D.

FIG. 10A, shows Representative confocal images of HLEB-3 cells transfected with various cataract-causing crystallin mutants. FIG. 10B, shows Representative confocal images of HeLa cells transfected with various cataract-causing crystallin mutants. Cells were transfected with various crystallin constructs for 4 h and cultured for an additional 24 h in fresh culture medium. Then the cells were treated with 10, 20 and 40 μM lanosterol in 1% (HLEB-3 cells) or 2% DMSO (HeLa cells) for 2 h and cultured for another 12 h. Cells treated with 1% (HLEB-3 cells) or 2% DMSO (HeLa cells) were used as the controls. Formation of intracellular aggregates of various crystallin proteins was visualized by fluorescence of GFP (green) and the nuclei were stained with Hoechst 33342 (blue). Typical intracellular aggregates are indicated by arrows. FIG. 10C, shows Concentration dependence of the aggregation-dissolving effects of lanosterol when assayed in HLEB-3 cells. FIG. 10D, shows Concentration dependence of the aggregation-dissolving effects of lanosterol when assayed in HeLa cells.

FIG. 11A, shows Human lens progenitor cells were transfected with mutant crystallin genes for 4 h, and then incubated in fresh culture medium for another 24 h. The cells were harvested and lysed. Supernatant and insoluble fractions were separated by centrifugation and analyzed by western blot analysis. LSS and crystallin fusion proteins were identified by antibodies against Flag and GFP tags, respectively. The lanosterol-treated group is highlighted by red boxes. Cells treated with 1% DMSO were used as a control. β-Actin was used as an internal protein loading control of total cell lysates (TCL). S, supernatant; P, insoluble fraction. FIG. 11B, shows Effect of DMSO (n=4) and cholesterol (n=7) on the size changes of αA-crystallin (Y118D) aggregates in human lens progenitor cells evaluated by single-particle tracking in live-cell imaging. FIG. 11C, shows Evaluation of the effect of lanosterol on the dissolution of crystallin aggregates by turbidity. Crystallin aggregates were formed by incubating 5 mg ml$^{-1}$ protein solution at 60° C. for 2 h (α-crystallins) or 37° C. for 48 h (β- and γ-crystallins) in the presence of 1 M guanidine chloride. The preformed aggregates were re-suspended in PBS at a final protein concentration of 0.2 mg ml$^{-1}$ and were treated with 500 μM sterols in 500 μM DPPC liposome and incubated at 37° C. for 24 h. Aggregates treated with 500 μM DPPC liposome only were used as the controls. FIG. 11D, shows Concentration-dependent effect of lanosterol on the re-dissolution of amyloid-like fibrils by αA-crystallin mutants evaluated by ThT fluorescence. Aggregates treated with 500 μM DPPC liposome only were used as the controls.

FIG. 12A, shows Lenses were placed above a grid and photographed. The degree of transparency was scored as 0, a clear lens and absence of opacification (gridlines clearly visible, a'); 1, a blurry lens and a slight degree of opacification (minimal clouding of gridlines, with gridlines still visible, b'); 2, a cloudy lens and presence of diffuse opacification involving almost the entire lens (moderate clouding of gridlines, with main gridlines visible, c'); or 3, an opaque lens and presence of extensive thick opacification involving the entire lens (total clouding of gridlines, with gridlines not seen at all, d'). FIG. 12B, shows Lanosterol reduced cataract severity and increased clarity in isolated cataractous rabbit lenses. Rabbit lenses (n=13) were dissected and incubated with lanosterol for 6 days and subsequently assessed for lens clarity and transparency. Pairs of photographs of each cataractous rabbit lens showing before and after treatment with scores underneath are shown. FIG. 12C, shows Lanosterol reduced cataract severity and increased lens clarity in dogs. Dog eyes with cataracts (n=7) were treated with lanosterol for 6 weeks and assessed for lens clarity and transparency. A pair of photographs of each study eye before and after treatment is shown with scores underneath. Three control eyes treated with vehicles alone are also presented.

DETAILED DESCRIPTION

Figure 1A:
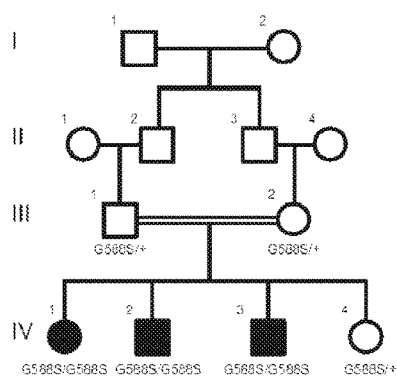
FIG. 1A, FIG. 1B, and FIG. 1C show identification of mutations in LSS causing congenital cataracts.
Figure 1A:
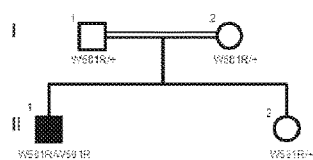

Reference will now be made in detail to specific embodiments of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In the following description, specific details are set forth in order to provide a thorough understanding of the present invention. The present invention may be practiced without some or all of these specific details. In addition, well-known features may not have been described in detail to avoid unnecessarily obscuring the invention.

The present invention relates to a method of and compositions for treating or preventing vision disorders that affect the normal structure of the eye in a subject having or at risk of developing such vision disorders, comprising administering to such subject a composition comprising a pharmaceutically acceptable carrier and a pharmaceutically effective amount of a sterol having the formula I. For example, an exemplary compound of the invention comprises administering to a patient an opthalmological pharmaceutically effective amount of lanosterol (3β-Hydroxy-8,24-lanostadiene; 8,24-Lanostadien-3β-ol).

In other embodiments, the present disclosure describes sterols and methods of using sterols. For example, the sterols of formula I are formulated in ophthalmic pharmaceutical compositions comprising a pharmaceutically acceptable ophthalmic carrier to inhibit crystallin protein aggregation.

In certain other embodiments, the present disclosure describes methods of using sterols of formula 1 to inhibit crystallin protein aggregation. In yet other embodiments, compounds of the invention are able to reverse aggregation of crystallin protein and inhibit further aggregation of crystallin protein.

Methods of Treating or Preventing Vision Disorders

The present invention provides ophthalmic pharmaceutical compositions and methods of using the present invention in preventing and/or treating vision disorders that affect the normal structure of the lens in the eye in a subject having or at risk of developing such vision disorders. As described herein, a vision disorder that affects the normal structure of the lens in the eye (referred herein as the phrase "vision disorder") refers to conditions that affect the structure of the lens as to cause vision dysfunction, such as changes to the clarity or rigidity of the lens of the eye. Such conditions include cataracts, presbyopia and nuclear sclerosis. In addition, vision disorders refer to retinal degeneration, such as Refsum disease, Smith-Lemli-Opitz syndrome (SLOS) and Schnyder crystalline corneal dystrophy (SCCD), abetalipoproteinemia and familial hypobetalipoproteinemia. In certain embodiments, the present invention provides compositions and methods of use thereof to alleviate or reverse crystalline protein aggregation. In alternative embodiments, there are provided compositions and methods for inhibiting, preventing and/or treating the disruption of intra- or inter-protein interactions that form the macro-structure essential for lens transparency and refractive index.

The term "cataract" as referred to in the present invention means a disease or condition that exhibits symptoms of causing cloudiness or opacity on the surface and/or the inside of the lens or inducing the swelling of the lens, and it includes both congenital cataract and acquired cataract (cf. PDR Staff, "PDR of Ophthalmic Medicines 2013", PDR Network, 2012). In some embodiments, the cataract is an age-related cataract, a diabetic cataract, a cataract associated with surgery, a cataract resulting from exposure to radiation, a cataract resulting from a genetic illness, a cataract resulting from an infection, or a cataract resulting from medication. In some embodiments, the individual has a hereditary form of cataract with early onset. Concrete examples of such are congenital cataract such as congenital pseudo-cataract, congenital membrane cataract, congenital coronary cataract, congenital lamellar cataract, congenital punctuate cataract, and congenital filamentary cataract; and acquired cataract such as geriatric cataract, secondary cataract, browning cataract, complicated cataract, diabetic cataract, traumatic cataract, and others inducible by electric shock, radiation, ultrasonic, drugs, systemic diseases, and nutritional disorders. Acquired cataract further includes postoperative cataract with symptoms of causing cloudiness in the posterior encapsulating a lens inserted to treat cataract.

Nuclear sclerosis refers to a condition, generally in older animals, that results similarly in opacity of the lens. It is an age-related change in the density of the crystalline lens nucleus that is caused by compression of older lens fibers in the nucleus by new fiber formation.

Presbyopia refers to a vision condition in which the crystalline lens of the eye loses its flexibility, which makes it difficult to focus on close objects.

In some embodiments, the invention provides a method of treating or preventing a vision disorder, the method comprising administering to an individual in need thereof an effective amount of a composition comprising a compound having a structural formula I. In some embodiments, the compound is a sterol having a structural formula I.

An individual "in need of" treatment according to the invention is an individual that is suffering from a vision disorder that affects the normal function of the lens in the eye. For example, the individual may have or is at risk for developing an age-related cataract or a cataract. Individuals at risk of developing a cataract include, but are not limited to, individuals with a family history of developing cataracts, individuals with a mutation linked to a cataract, individuals exposed to radiation, diabetics, and the like. For example, in one aspect, the individual has been diagnosed with cataract in one eye, and the compound is administered to prevent or slow cataract formation in the contralateral eye. Similarly, an individual "in need of" treatment according to the invention is an individual that may have or is at risk for developing presbyopia. Similarly, an individual "in need of" treatment according to the invention is an individual that has or is at risk for developing nuclear sclerosis. Preferably the individual is human, however, animals that suffer from or who are at risk for an eye disease (animals in need of treatment) can also be identified by one skilled in the art. Mammals in need of treatment, such as cats, dogs, pigs, horses, cows and rodents can be identified. Additionally, animals such as avians, reptiles, amphibians, and fish that are in need of treatment can be identified.

"Treating" a vision disorder does not require a 100% abolition or reversal of a vision disorder. In some embodiments, "treating" vision disorders according to inventive method alleviates, inhibits, prevents and/or reverses dysfunction of the lens, e.g., opacity or inflexibility of the lens by, e.g., at least about 5%, at least about 10% or at least about 20% compared to levels observed in the absence of the inventive composition or method (e.g., in a biologically-matched control subject or specimen that is not exposed to the invention composition or compound of the inventive method). In some embodiments, dysfunction (such as cataract formation, opacity or crystalline aggregation on or in the lens) is treated by at least about 30%, at least about 40%, at least about 50%, or at least about 60%, at least about 70%, at least about 80%, at least about 90%, or more (about 100%) compared to lens dysfunction in the absence of the compound of the inventive method. Lens dysfunction, such as opacity or cloudiness or cataracts, generally are detected using any of a number of optic tests including, but not limited to, visual acuity testing, ophthalmoscopy, slit-lamp examination, keratometry, tonometry, contrast testing, glare sensitivity, wavefront mapping.

Similarly, "prevention" does not require 100% inhibition or deterrence of a vision disorder. For example, any reduction in cloudiness or opacity, or deceleration of cataract progression constitutes a beneficial biological effect in a subject. Also exemplary, any decrease in crystalline aggregation in the lens of an eye constitutes a beneficial biological effect. In this regard, the invention reduces the vision disorder, e.g., at least about 5%, at least about 10% or at least about 20% compared to levels observed in the absence of the inventive method (e.g., in a biologically-matched control subject or specimen that is not exposed to the compound of the inventive method). In some embodiments, the vision disorder is reduced by at least about 30%, at least about 40%, at least about 50%, or at least about 60%, at least about 70%, at least about 80%, at least about 90%, or more (about 100%).

Inhibiting, preventing or reversal of dysfunction does not require a 100% inhibition, prevention, abolition or reversal. For example, any inhibition of aggregation constitutes a beneficial biological effect in a subject. In this regard, the invention inhibits a vision disorder that affects the normal function of the lens of the eye in a subject, e.g., at least about 5%, at least about 10% or at least about 20% compared to levels observed in the absence of the inventive method (e.g., in a biologically-matched control subject or specimen that is not exposed to the compound of the inventive method). In some embodiments, the vision disorder is inhibited, prevented and/or reversed by at least about 30%, at least about 40%, at least about 50%, or at least about 60%. In some embodiments, the inventive method inhibits amyloid formation by at least about 70%, at least about 80%, at least about 90%, or more (about 100%) compared to amyloid formation in the absence of the compound of the inventive method.

An "effective amount" of an ophthalmic pharmaceutical composition comprising a compound of formula 1 is an amount that inhibits, prevents or reverses dysfunction of the lens in an individual. An ophthalmic pharmaceutical composition of the present invention is being administered to a subject in need thereof at an effective amount to treat the vision disorder. As used herein, "therapeutically effective amount" means a dose that alleviates at least one of the signs, symptoms, or causes of a vision disorder, or any other desired alteration of a biological system. In preventative applications, the term "prophylactically effective amount" means a dose administered to a patient susceptible to or otherwise at risk of a particular disease, which may be the same or different dose as a therapeutically effective amount. The effective amount of the composition for a particular individual can depend on the individual, the severity of the condition of the individual, the type of formulation being applied, the frequency of administration, and the duration of the treatment. In accordance with the present invention, administration of an ophthalmic pharmaceutical formulation of the present invention such as, e.g., lanosterol, even at relatively low concentrations in liquid drops, e.g., at least $10^{-9}$ M, at least 0.5 to $1\times10^{-8}$ M, at least 0.5 to $1\times10^{-7}$ M, at least 0.5 to $1\times10^{-6}$ M, at least 0.5 to $1\times10^{-5}$ M, at least 0.5 to $1\times10^{-4}$ M, or at least 0.5 to $1\times10^{-3}$ M, or any concentration falling in a range between these values (e.g., $10^{-9}$ M to $10^{-3}$ M), may reverse such vision disorders with only one, two, three or multiple, daily applications and does so rapidly.

Route of Administration

As will be understood by those skilled in the art, the most appropriate method of administering a compound to a subject is dependent on a number of factors. In various embodiments, the compound according to the invention is administered locally to the eye, e.g., topically, subconjunctivally, retrobulbarly, periocularly, subretinally, suprachoroidally, or intraocularly.

Pharmaceutical compositions that are particularly useful for administration directly to the eye include aqueous solutions and/or suspensions formulated as eye drops and thickened solutions and/or suspensions formulated as ophthalmic gels (including gel-forming solutions) or ointments, which is an ophthalmic solution, ophthalmic ointment, ophthalmic wash, intraocular infusion solution, wash for anterior chamber, internal medicine, injection, or preservative for extracted cornea. Other dosage forms for ophthalmic drug deliver include ocular inserts, intravitreal injections and implants. Injectable solutions can be directly injected into the cornea, crystalline lens and vitreous or their adjacent tissues using a fine needle. The composition also can be administered as an intraocular perfusate.

Additional contemplated routes of administration include, but are not limited to, one or more of: oral (e.g., as a tablet, capsule, or as an ingestible solution), mucosal (e.g., as a nasal spray or aerosol for inhalation), nasal, parenteral (e.g., by an injectable form), gastrointestinal, intraspinal, intraperitoneal, intramuscular, intravenous, intrauterine, intradermal, intracranial, intratracheal, intravaginal, intracerebroventricular, intracerebral, subcutaneous, transdermal, rectal, buccal, epidural and sublingual.

In some embodiments, the mode for delivery of a composition of the invention to the eye is via a contact lens. The lens may be provided pre-treated with the desired compound. Alternatively, the lens is provided in a kit with components for preparing a coated lens, which are provided as lyophilized powders for reconstitution or as concentrated or ready-to-use solutions. The compositions can be provided as kits for single or multi-use.

In some embodiments, the mode for delivery of a composition of the invention to the eye is via an ophthalmic rod (Gwon et al., Ophthalmology. 1986 September; 93(9 Suppl): 82-5). In some embodiments, the mode for delivery of a composition of the invention to the eye is via an intraocular lens-hydrogel assembly (Garty et al., Invest Ophthalmol Vis Sci, 2011 Aug. 3; 52(9):6109-16).

Dose

The composition comprising the compound is provided in a therapeutically effective amount that achieves a desired biological effect at a medically-acceptable level of toxicity. The dosage of the compositions may vary depending on the route of administration and the severity of the disease. The dosage may also be adjusted depending on the body weight, age, sex, and/or degree of symptoms of each patient to be treated. The precise dose and route of administration will ultimately be at the discretion of the attendant physician or veterinarian. It will be appreciated that it may be necessary to make routine variations to the dosage depending on the age and weight of the patient as well as the severity of the condition to be treated. The frequency of administration depends on the formulation and the aforementioned parameters. For example, it may be desirable to apply eye drops at least once per day, including 2, 3, 4, or 5 times per day.

Persons of ordinary skill can easily determine optimum dosages, dosing methodologies and repetition rates. Optimum dosages may vary depending on the relative potency of the particular pharmaceutical composition and the method of administration. Acceptable dosages can generally be estimated based on EC50 (effective concentration for 50% of the test group) found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the therapeutic compositions described herein are administered in maintenance doses, ranging from 0.01 μg to 100 g per kg of body weight, once or more daily, to once every 20 years. Exemplary doses of the compounds for administration to a human (of approximately 70 kg body weight) via systemic route are 0.1 mg to 5 g, e.g., 1 mg to 2.5 g of the compound per unit dose.

Preferred concentrations of the compound of formula I range from about 1 μg/ml to 500 μg/ml, for example, about 1 μg/ml, about 2 μg/ml, about 3 μg/ml, about 4 μg/ml, about 5 μg/ml, about 10 μg/ml, about 20 μg/ml, about 30 μg/ml, about 40 μg/ml, about 50 μg/ml, about 60 μg/ml, about 70 μg/ml, about 80 μg/ml, about 90 μg/ml, about 100 μg/ml, about 120 μg/ml, about 140 μg/ml, about 160 μg/ml, about 180 μg/ml, about 200 μg/ml, about 250 μg/ml, about 300

µg/ml, about 350 µg/ml, about 400 µg/ml, about 450 µg/ml, or about 500 µg/ml. The inhibitor may be provided in combination with other pharmaceutically active agents.

The pharmaceutical compositions described herein can be administered as a single dose or in multiple doses; administered either as individual therapeutic agents or in combination with other therapeutic agents; and combined with conventional therapies, which may be administered sequentially or simultaneously. In one embodiment of the invention, daily dosages in human and/or animal therapy of the present ophthalmic formulations are about 1 drop per eye, about 2 drops per eye, about 3 drops per eye, about 4 drops per eye, about 5 drops per eye, about 6 drops per eye, about 7 drops per eye, about 8 drops per eye, about 9 drops per eye, about 10 drops per eye, about 11 drops per eye, about 12 drops per eye or more than about 12 drops per eye. In another embodiment of the invention, daily administration schedule for the present ophthalmic formulations in human and/or animal therapy is about 1 time per day, about 2 times per day, about 3 times per day, about 4 times per day, about 5 times per day, about 6 times per day, about 7 times per day, about 8 times per day, about 9 times per day, about 10 times per day, about 11 times per day, about 12 times per day or more than about 12 times per day. Dosages can be standardized for instance by means of a standard pharmacopeial medicinal dropper of 3 mm in external diameter, which when held vertically delivers 20 drops of water of total weight of 0.9 to 1.1 grams at 25° C.

When administered according to the dosage schedule described above, the treatment regimen in humans and/or animals can continue indefinitely or until no further improvement is observed. Alternately, the treatment regimen can last for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 60 days, 70 days, 80 days, 90 days, 100 days, 150 days, 200 days, 250 days, 300 days, 400 days, 500 days, 750 days, 1000 days or more than 1000 days.

Compounds Effective in Treating or Preventing Cataract

In various embodiments, the compound of the inventive method or composition is lanosterol having a compound of formula I:

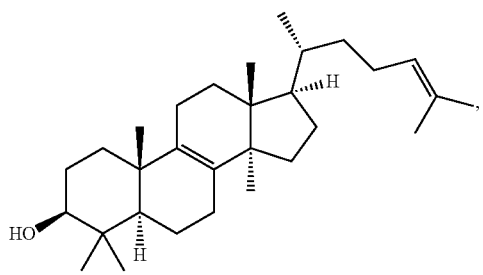 [SMILES: CC(C)=CCC[C@@H](C)[C@H]1CC[C@@]2(C)C3=C(CC[C@]12C)[C@@]1(C)CC[C@H](O)C(C)(C)[C@@H]1CC3]

or a prodrug or pharmaceutically acceptable salt thereof.

For example, the compound of the inventive method or composition is lanosterol; a prodrug or pharmaceutically acceptable salt thereof. In one embodiment, the compound is lanosterol. In another embodiment, any prodrug or pharmaceutically acceptable salt of the above compounds are contemplated to be within the scope of the invention.

Pharmaceutical Compositions

In some embodiments of the invention, pharmaceutical compositions of one or more therapeutic compounds can be prepared by formulating one or more of these therapeutic compounds in a pharmaceutically acceptable carrier. As used herein, "pharmaceutically or therapeutically acceptable carrier" refers to a carrier medium which does not interfere with the effectiveness of the biological activity of the active ingredients and which is not toxic to the host or patient. The type of carrier which is used in the pharmaceutical preparation will depend on the method by which the therapeutic compounds are to be administered. Many methods of preparing pharmaceutical compositions for various routes of administration are well known in the art.

As used herein, "pharmaceutically acceptable ophthalmic carrier" refers to a pharmaceutically acceptable excipient, carrier, binder, and/or diluent for delivery of the compound of the structural formula 1 directly or indirectly to, on or near the eye. Accordingly, the invention further comprises a composition comprising the compound of the structural formula I and a pharmaceutically acceptable ophthalmic carrier.

Optionally, the composition includes a free acid, free base, salt (e.g., an acid or base addition salt), hydrate or prodrug of the compound of structural formula I. The phrase "pharmaceutically acceptable salt" or "pharmaceutically acceptable acid," as used herein, refers to pharmaceutically acceptable organic or inorganic salts or acids, respectively, of a compound of Formula I. The counter ion may be any organic or inorganic moiety that stabilizes the charge on the parent compound. Furthermore, a pharmaceutically acceptable salt (or acid) may have more than one charged atom in its structure. Instances where multiple charged atoms are part of the pharmaceutically acceptable salt (or acid) can have multiple counter ions. Hence, a pharmaceutically acceptable salt (acid) can have one or more charged atoms and/or one or more counter ion.

Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion.

The prodrug is a material that includes the compound of structural formula I covalently bound to a carrier moiety. The carrier moiety can be released from the compound of structural formula 1, in vitro or in vivo to yield compound of structural formula I. Prodrug forms are well known in the art as exemplified in Sloan, K. B., Prodrugs, M. Dekker, New York, 1992; and Testa, B. and Mayer, J. M., Hydrolysis in drug and prodrug metabolism: chemistry, biochemistry, and enzymology, Wiley-VCH, Zurich, 2003.

In some embodiments of the invention, pharmaceutical compositions are prepared by dissolving the invention composition in an appropriate solvent. Appropriate solvents include, but are not limited to, water, saline solution (for example, NaCl), buffered solutions, ointments, gels or other solvents. In certain embodiments, the solvents are sterile.

Aqueous solutions and diluents for suspensions that are used in preparation of eye drops can include distilled water, physiological saline, and the like. These pharmaceutical compositions can be formulated by admixing, diluting or dissolving the compound, optionally, with appropriate pharmaceutical additives such as excipients, disintegrators, binders, lubricants, diluents, buffers, antiseptics, moistening agents, emulsifiers, dispersing agents, stabilizing agents and dissolving aids in accordance with conventional methods and formulating in a conventional manner depending upon the dosage form. Non-aqueous solutions and diluents for suspensions can include edible (eg vegetable) oil, liquid paraffin, mineral oil, propylene glycol, p-octyldodecanol, polysorbate, macrogols, aluminum monostearate as well as similar solvents.

Various additives may be contained in eye drops, ophthalmic gels and/or ophthalmic ointments as needed. These can include additional ingredients, additives or carrier suitable for use in contact on or around the eye without undue toxicity, incompatibility, instability, irritation, allergic response, and the like. Additives such as solvents, bases, solution adjuvants, suspending agents, thickening agents, emulsifying agents, stabilizing agents, buffering agents, isotonicity adjusting agents, pH-adjusting agents, chelating agents, soothing agents, preservatives, corrigents, flavoring agents, coloring agents, excipients, binding agents, lubricants, surfactants, absorption-promoting agents, dispersing agents, preservatives, solubilizing agents, and the like, can be added to a formulation where appropriate.

For example, eye drops can be formulated by dissolving the compound in sterilized water in which a surface active agent is dissolved and optionally adding appropriate pharmaceutical additives such as a preservative, a stabilizing agent, a buffer, an antioxidant and a viscosity improver.

For example, buffering agents are added to keep the pH constant and can include pharmaceutically acceptable buffering agents such as borate buffer, citrate buffer, tartrate buffer, phosphate buffer, acetate buffer or a Tris-HCl buffer (comprising tris(hydroxymethyl) aminomethane and HCl). For example, a Tris-HCl buffer having pH of 7.4 comprises 3 g/l of tris-(hydroxymethyl)-aminomethane and 0.76 g/l of HCl. In yet another aspect, the buffer is 10× phosphate buffer saline ("PBS") or 5×PBS solution. Buffering agents are included in an amount that provides sufficient buffer capacity for the expected physiological conditions.

Other buffers include, but are not limited to, buffers based on HEPES (N-{2-hydroxyethyl}peperazine-N'-{2-ethanesulfonic acid}) having $pK_a$ of 7.5 at 25° C. and pH in the range of about 6.8-8.2; BES (N,N-bis{2-hydroxyethyl}2-aminoethanesulfonic acid) having $pK_a$ of 7.1 at 25° C. and pH in the range of about 6.4-7.8; MOPS (3-{N-morpholino}propanesulfonic acid) having $pK_a$ of 7.2 at 25° C. and pH in the range of about 6.5-7.9; TES (N-tris{hydroxymethyl}-methyl-2-aminoethanesulfonic acid) having $pK_a$ of 7.4 at 25° C. and pH in the range of about 6.8-8.2; MOBS (4-{N-morpholino}butanesulfonic acid) having $pK_a$ of 7.6 at 25° C. and pH in the range of about 6.9-8.3; DIPSO (3-(N,N-bis{2-hydroxyethyl 1 amino)-2-hydroxypropane)) having $pK_a$ of 7.52 at 25° C. and pH in the range of about 7-8.2; TAPS ({(2-hydroxy-3{tris(hydroxymethyl)methylamino}-1-propanesulfonic acid)) having $pK_a$ of 7.61 at 25° C. and pH in the range of about 7-8.2; TAPS ({(2-hydroxy-1,1-bis(hydroxymethyl)ethyl)aminol-1-propanesulfonic acid)) having $pK_a$ of 8.4 at 25° C. and pH in the range of about 7.7-9.1; TABS (N-tris(hydroxymethyl)methyl-4-aminobutanesulfonic acid) having $pK_a$ of 8.9 at 25° C. and pH in the range of about 8.2-9.6; AMPSO (N-(1,1-dimethyl-2-hydroxyethyl)-3-amino-2-hydroxypropanesulfonic acid)) having $pK_a$ of 9.0 at 25° C. and pH in the range of about 8.3-9.7; CHES (2-cyclohexylamino)ethanesulfonic acid) having $pK_a$ of 9.5 at 25° C. and pH in the range of about 8.6-10.0; CAPSO β-(cyclohexylamino)-2-hydroxy-1-propanesulfonic acid) having $pK_a$ of 9.6 at 25° C. and pH in the range of about 8.9-10.3; and CAPS β-(cyclohexylamino)-1-propane sulfonic acid) having $pK_a$ of 10.4 at 25° C. and pH in the range of about 9.7-11.1.

In addition to a buffer, isotonizers can be added to eye drops to make the preparation isotonic with the tear. Isotonizers include, but are not limited to, sugars such as dextrose, glucose, sucrose and fructose; sugar alcohols such as mannitol and sorbitol; polyhydric alcohols such as glycerol, polyethylene glycol and propylene glycol; and salts such as sodium chloride, sodium citrate, benzalkonium chloride, phedrine chloride, potassium chloride, procaine chloride, chloram phenicol, and sodium succinate. Isotonizers are added in an amount that makes the osmotic pressure of the eye drop equal to that of the tear.

Preservatives can be added to maintain the integrity of the eye drop and/or ophthalmic ointment. Examples of preservatives include, but are not limited to, sorbic acid, benzalkonium chloride, benzododecinium bromide, parabens, chlorobutanol, benzylic alcohol, phenylethyl alcohol, edentate disodium, sorbic acid, polyquaternium-1, or other agents known to those skilled in the art.

In some embodiments, thickeners are used to increase the viscosity of ophthalmic preparations such as eye drops, ophthalmic gels and/or ophthalmic ointments. Thickeners that can be used include, but are not limited to, glycerol, polyethylene glycol, carboxymethyl cellulose and carboxyvinyl polymers.

In addition to the above, in some embodiments, it is desirable to use additional agents which include, but are not limited to, stabilizers such as sodium sulfite, sodium carbonate, and propylene glycol; antioxidants such as ascorbic acid, sodium ascorbate, butylated hydroxy toluene (BHT), butylated hydroxyanisole (BHA), tocopherol, sodium thiosulfate; and/or chelating agents such as ethylene-diamine-tetra-acetic acid (EDTA), ethylene glycol-bis-(2-aminoethyl)-N,N,N,N-tetraacetic acid (EGTA) and sodium citrate.

Eye drops, ophthalmic gels and/or ophthalmic ointments can be prepared by aseptic manipulation or alternatively sterilization is performed at a suitable stage of preparation. For example, a sterile pharmaceutical composition can be prepared by mixing sterile ingredients aseptically. Alternatively, the sterile pharmaceutical composition can be prepared by first mixing the ingredients then sterilizing the final preparation. Sterilization methods can include, but are not limited to, heat sterilization, irradiation and filtration.

Ophthalmic ointments (eye ointments) can be aseptically prepared by mixing the active ingredient into a base that is used for preparation of eye ointments followed by formulation into pharmaceutical preparations with any method known in the art. Typical bases for eye ointments are exemplified by vaseline, jelene 50, plastibase and macrogol. In addition, surfactants may be added to increase hydrophilia.

A number of effective methods for controlled release of an active agent are available. See, for example, Wagh V. D., Inamdar B., Samanta M. K., Polymers used in ocular dosage form and drug delivery systems. Asian J Pharm 2, 2008, 12-17 and the literature references cited therein, the contents of which are incorporated herein by reference. The use of polymers (e.g., cellulose derivatives such as hydroxypropylmethylcellulose (HPMC) and hydroxypropylcellulose (HPC), poly (acrylic acid) (PAA), polyacrylates, cyclodextrins and natural gums, polyorthoesters (POEs) and mucoadhesive polymers); semisolids such as gels, films and other inserts; resins such as ion exchange resins; iontophoretic delivery; and colloidal particles such as microspheres and nanoparticles, are specifically contemplated.

The compounds of the invention may also be provided in combination with other therapeutic agents. In some embodiments, the compounds of the invention may be co-formulated with other active agents, including, but not limiting to, anti-infective agents, antibiotics, antiviral agents, anti-fungal, anti-protozoal agent, anti-inflammatory drugs, antiallergic agents including anti-histamines, artificial tears vasoconstrictors, vasodilators, local anesthetics, analgesics, intraocular pressure-lowering agents, immunoregulators, anti-oxidants, vitamins and minerals, an enzyme inhibitor or alternatively, proteases and peptidases, a cytokine inhibitor, and the like.

In various embodiments, the compounds of the invention may also be provided in combination with an ocular therapeutic selected from the group consisting of Acular (ketorolac tromethamine ophthalmic solution) 0.5%, Acuvail (ketorolac tromethamine), AK-Con-A (naphazoline ophthalmic), Akten (lidocaine hydrochloride), Alamast, Alphagan (brimonidine), Alrex, Astepro (azelastine hydrochloride nasal spray), AzaSite (azithromycin), Bepreve (bepotastine besilate ophthalmic solution), Besivance (besifloxacin ophthalmic suspension), Betaxon, BSS Sterile Irrigating Solution, Cosopt, Durezol (difluprednate), Eylea (aflibercept), Lotemax, Lucentis (ranibizumab), Lumigan (bimatoprost ophthalmic solution), Macugen (pegaptanib), Ocuflox (ofloxacin opthalmic solution) 0.3%, OcuHist, Ozurdex (dexamethasone), Quixin (levofloxacin), Rescula (unoprostone isopropyl ophthalmic solution) 0.15%, Restasis (cyclosporine ophthalmic emulsion), Salagen Tablets, Travatan (travoprost ophthalmic solution), Valcyte (valganciclovir HCl), Viroptic, Vistide (cidofovir), Visudyne (verteporfin for injection), Vitrasert Implant, Vitravene Injection, ZADITOR, Zioptan (tafluprost ophthalmic solution), Zirgan (ganciclovir ophthalmic gel), Zymaxid (gatifloxacin ophthalmic solution), Atropine, Flurbiprofen, Physostimine, Azopt, Gentamicin, Pilocarpine, Bacitracin, Goniosol, Polymyxin B, Betadine, Gramicidin, Prednisolone, Betaxolol, Humorsol, Proparacaine, Betoptic, Hylartin, Propine, Brinzolamide, Hypertonic NaCl, Puralube, BSS, Indocycanine Green, Rose Bengal, Carbachol, Itraconazole, Sodium Hyaluronate, Cefazolin, Latanoprost, Suprofen, Celluvisc, Mannitol, Terramycin, Chloramphenicol, Methazolamide, Timolol, Ciloxan, Miconazole, Tobramycin, Ciprofloxacin, Miostat, Triamcinolone, Cosopt, Muro 128, Trifluridine, Demecarium, Neomycin, Tropicamide, Dexamethasone, Neptazane, Trusopt, Dipivefrin, Ocuflox, Vidarabine, Dorzolamide, Ofloxacin, Vira-A, Epinephrine, Oxytetracycline, Viroptic, Fluorescein, Phenylephrine, and Xalatan.

Kits

Some embodiments of the invention relate to kits for preventing and/or ameliorating one or more symptoms associated with an eye disease. The kits can comprise one or more containers that contain one or more of the therapeutic compounds described herein. The compounds can be present in the container as a prepared pharmaceutical composition, or alternatively, the compounds can be unformulated. In such embodiments, the kit can include the unformulated compounds in a container that is separate from the pharmaceutically acceptable carrier. Prior to use, the compound in diluted or otherwise mixed with the pharmaceutically acceptable carrier.

Some embodiments of the kits provided herein also comprise instructions which describe the method for administering the pharmaceutical composition in such a way that one or more symptoms associated with an eye disease which includes, but is not limited to, retinal degeneration, presbyopia, cataracts and/or nuclear sclerosis of the eye lens. In some embodiments, the instructions also describe the procedure for mixing the therapeutic compounds contained in the kit with ophthalmic pharmaceutically acceptable carriers.

In some embodiments of the invention, the container that comprises the therapeutic compounds described herein is a container which is used for ophthalmic administration. In certain embodiments, the container is a dropper for administering eye drops. In other embodiments, the container is a tube for administering an ophthalmic gel or an ophthalmic ointment.

Some embodiments of this invention are further illustrated by the following examples that should not be construed as limiting. It will be appreciated by those of skill in the art that the techniques disclosed in the examples which follow represent techniques discovered by the inventor to function well in the practice of the embodiments of the invention described herein, and thus can be considered to constitute preferred modes for the practice of these embodiments. Those of skill in the art will, however, in light of the present disclosure, appreciate that many changes can be made in the specific embodiments which are disclosed herein and still obtain a like or similar result without departing from the spirit and scope of the invention.

Devices

Some embodiments of the invention relate to devices for administering the invention sterol to a subject. In some embodiments, the devices include an interior portion, cavity or reservoir that contains the invention sterol formulated in a pharmaceutically acceptable carrier. In such embodiments, the pharmaceutically carriers include, but are not limited to, solutions, gels, and ointments. In certain embodiments, the interior portion, cavity or reservoir contains one or more of the invention sterol-containing pharmaceutical preparations described herein.

In some embodiments, the devices contemplated herein also comprise an applicator that is coupled to the interior portion, cavity or reservoir of the device. The applicator can be cylindrical, conical or any other shape that permits the invention sterol-containing pharmaceutical preparation to be delivered from the interior portion, cavity or reservoir to the eye. In a preferred embodiment, the applicator is a tapered cylinder wherein the wide end is coupled to the interior portion, cavity or reservoir and the tapered end forms the exit opening for passage of the invention sterol-containing pharmaceutical preparation to the eye.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are intended to illustrate but not to limit the invention in any manner, shape, or form, either explicitly or implicitly. While they are typical of those mat might be used, other procedures, methodologies, or techniques known to those skilled in the art may alternatively be used.

Example 1

The human lens is comprised largely of crystallin proteins assembled into a highly ordered, interactive macro-structure essential for lens transparency and refractive index. Any disruption of intra- or inter-protein interactions will alter this delicate structure, exposing hydrophobic surfaces, with consequent protein aggregation and cataract formation. Cataracts are the most common cause of blindness worldwide, affecting tens of millions of peoplel, and currently the only treatment is surgical removal of cataractous lenses. The precise mechanisms by which lens proteins both prevent aggregation and maintain lens transparency are largely unknown. Lanosterol is an amphipathic molecule enriched in the lens. It is synthesized by lanosterol synthase (LSS) in a key cyclization reaction of a cholesterol synthesis pathway. Here we identify two distinct homozygous LSS missense mutations (W581R and G588S) in two families with extensive congenital cataracts. Both of these mutations affect highly conserved amino acid residues and impair key catalytic functions of LSS. Engineered expression of wild-type, but not mutant, LSS prevents intracellular protein aggregation of various cataract-causing mutant crystallins. Treatment by lanosterol, but not cholesterol, significantly decreased preformed protein aggregates both in vitro and in cell-transfection experiments. We further show that lanosterol treatment could reduce cataract severity and increase transparency in dissected rabbit cataractous lenses in vitro and cataract severity in vivo in dogs. Our study identifies lanosterol as a key molecule in the prevention of lens protein aggregation and points to a novel strategy for cataract prevention and treatment.

Cataracts account for over half of all cases of blindness worldwide, with the only established treatment involving surgical removal of the opacified lens. In developed nations, cataract surgeries amount to a significant portion of healthcare costs owing to the sheer prevalence of the disease among ageing populations. In addition, there is major morbidity associated with cataracts in developing countries, where there is limited access to surgical care.

High concentrations of crystallin proteins in lens fibres contribute to lens transparency and refractive properties[2]. The crystallin superfamily is composed of a-, b- and c-crystallins, which are some of the most highly concentrated intracellular proteins in the human body. Protein aggregation is the single most important factor in cataract formation[3]. Factors that lead to protein aggregation include mutations in crystallin proteins, which are known to cause congenital cataracts, or oxidative stress, which in turn contributes to age-related cataracts. However, the precise mechanisms by which lens proteins maintain transparency or cause opacification are not completely understood.

Lanosterol synthase (2,3-oxidosqualene-lanosterol cyclase, LSS; EC 5.4.99.7) is encoded by the LSS gene. The LSS protein catalyses the conversion of (S)-2,3-oxidosqualene to lanosterol, which is a key early rate-limiting step in the biosynthesis of cholesterol, steroid hormones, and vitamin D (ref. 4). LSS was found to be expressed in the lens[5]. It was previously reported that the specific combination of hypomorphic mutations on LSS and FDFT1 (farnesyl diphosphate farnesyl transferase 1) could decrease cholesterol levels in the lens and result in cataracts in Shumiya cataract rats (SCR)[6]. Here we identify novel homozygous mutations in the LSS gene in two consanguineous families and investigate the ability of lanosterol to alleviate protein aggregation and cataract formation.

Figure 1B:
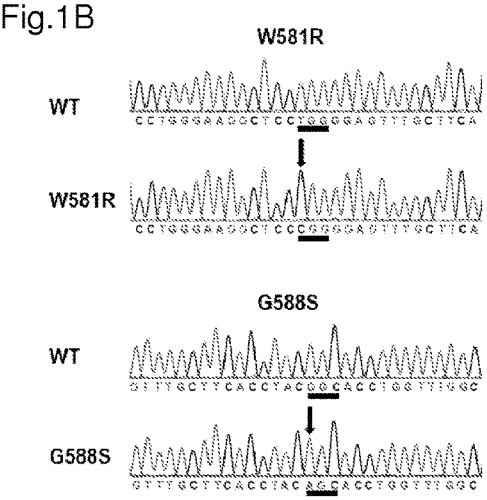
Figure 1C:
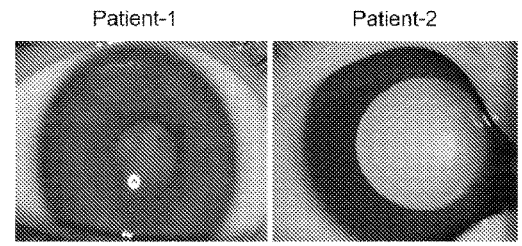
Figure 6A:
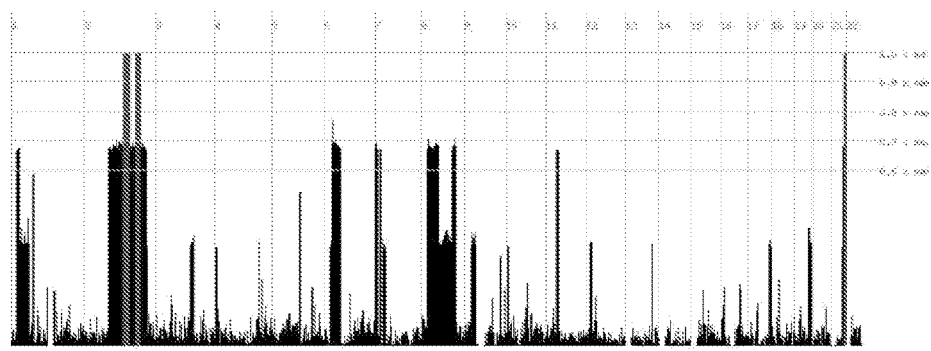
FIG. 6A shows homozygosity mapper plots the genome-wide homozygosity as bar charts. To emphasize regions of interest, any score higher than 80% of the maximum score reached in this project is coloured in red.
Figure 6B:
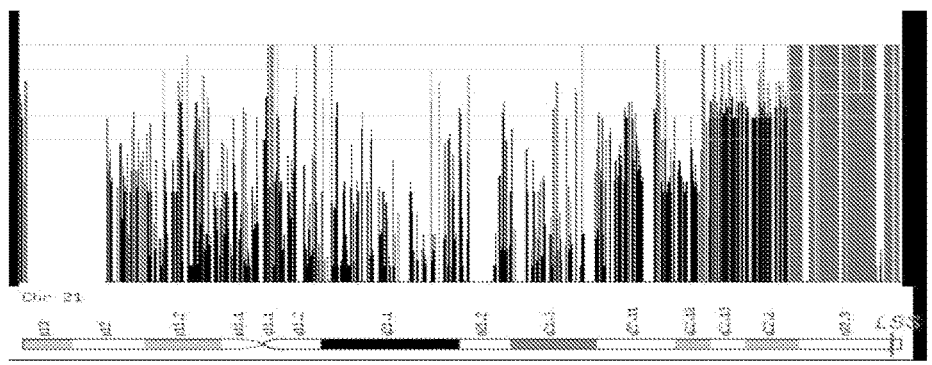
FIG. 6B shows the homozygosity scores were plotted against the physical position on chromosome 21, which contains the LSS gene. Red bars indicate regions with highest scores. The right side of the chromosome contains a long continuous homozygous region, where the LSS gene is located.

Three children with severe congenital cataract from a consanguineous family of Caucasian descent (FIG. 1A) were identified. Whole-exome sequencing was performed to an average of no less than 55-fold depth coverage on the target region (Table 1a) in order to identify the causal mutation. On average, 60,800-80,800 SNPs were detected in each exome (Table 1b). Using a consanguineous recessive model and filtering against common variants (minor allele frequency 0.0.5%) in public databases including dbSNP and the 1000 Genomes Project, as well as mutation function predictions (predicted by SIFT[7], Polyphen2[8], Phylop[9] and Mutationtaster[10]), we narrowed down potential candidate gene variants and identified a variant (G588S) in LSS on chromosome 21 as the most likely candidate (Table 1c). Three affected children were homozygous for the GRA transition (G588S) in LSS, (GRch37/hg19: chr21: 47615645; NM_001001438.2: c.1762G.A, NM_001001438.1: p.G588S), while the unaffected father, mother and remaining child were heterozygous for the change (FIG. 1A, FIG. 1B). Whole-genome SNP genotyping identified three long continuous homozygous regions in this family by Homozygosity Mapper[11] (chr2:q22.1-q24.1, chr2: q31.1-q32.1 and chr21:q22.3; —FIG. 6A and Table 1d). The LSS gene was located in one of the homozygous regions on chromosome 21 (FIG. 6B). Furthermore, we screened for mutations in the LSS gene in 154 families with congenital cataracts and identified another homozygous mutation, W581R (GRch37/hg19: chr21:47615666; NM_001001438.2:c.1741T.C, NM_001001438.1: p.W581R), in a second consanguineous family (FIG. 1A, FIG. 1B, FIG. 1C). These two mutations were absent in 11,000 control chromosomes.

Figure 3A:
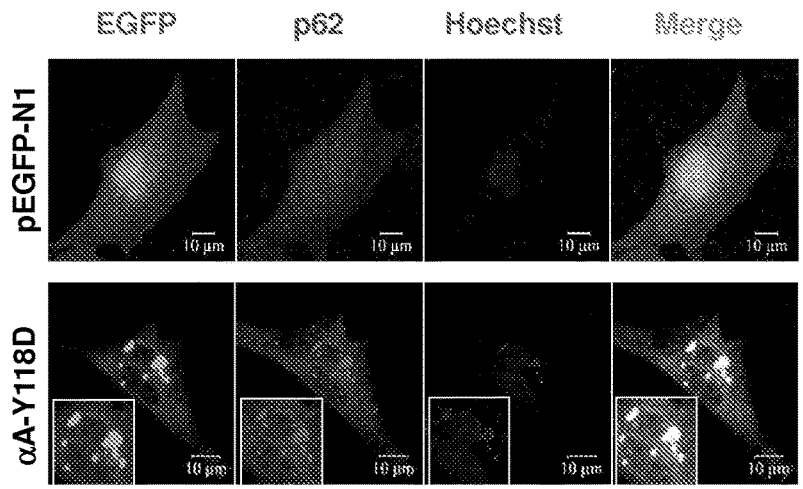
FIG. 3A, FIG. 3B, FIG. 3C, FIG. 3D, FIG. 3E, FIG. 3F, FIG. 3G, FIG. 3H, and FIG. 3I show lanosterol reduced intracellular aggregation of various crystallin mutant proteins.
Figure 3B:
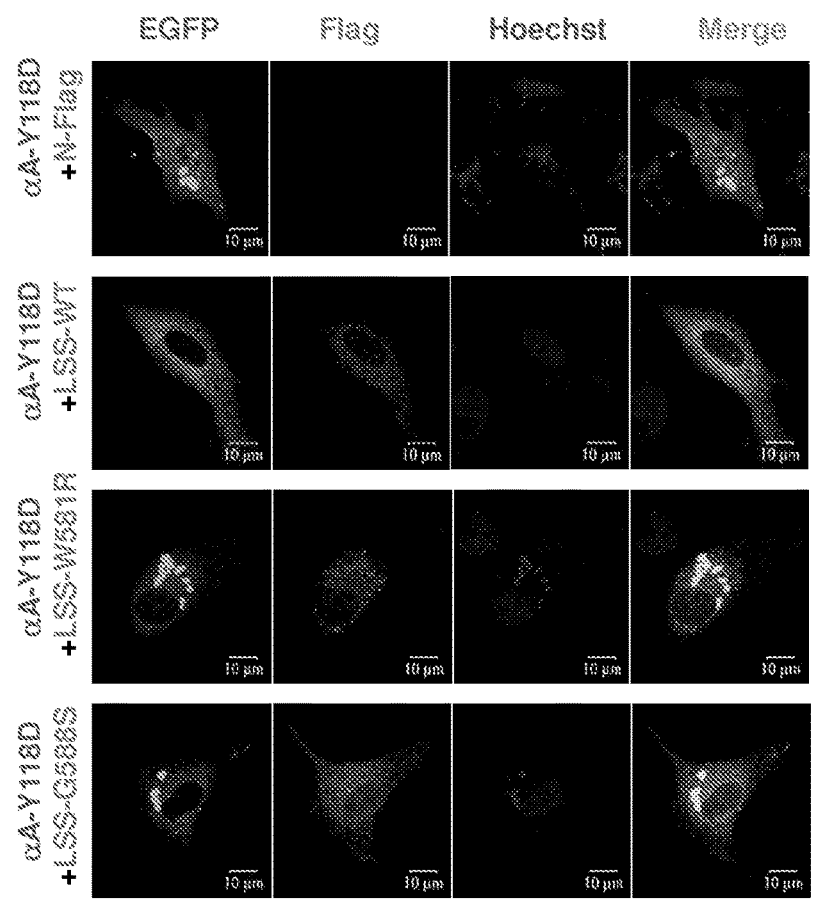
Figure 3C:
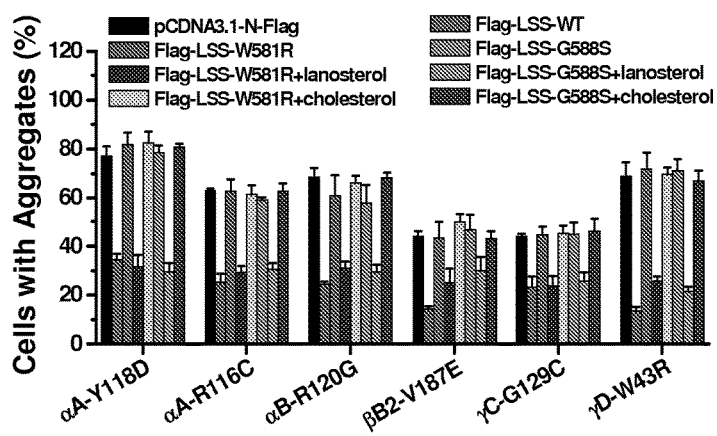
Figure 3D:
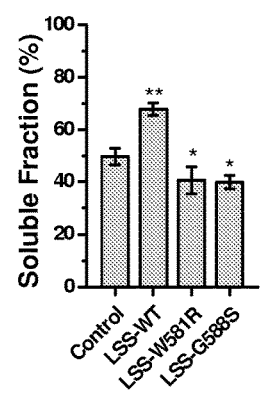
Figure 3E:
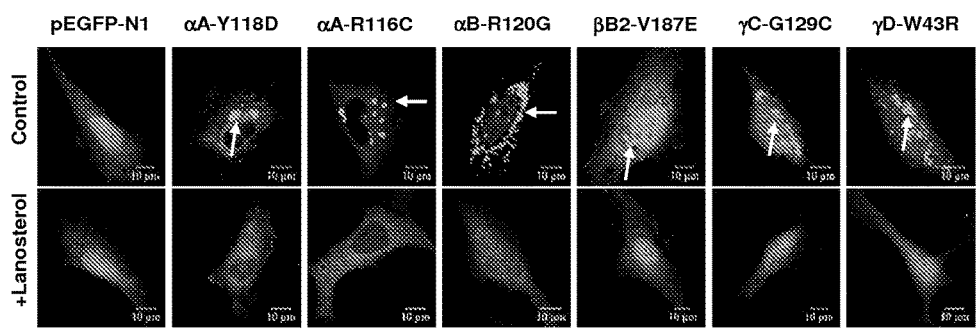
Figure 3F:
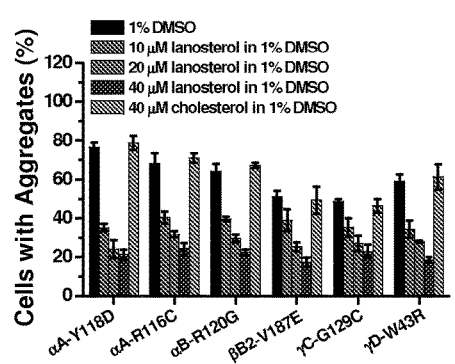
Figure 7:
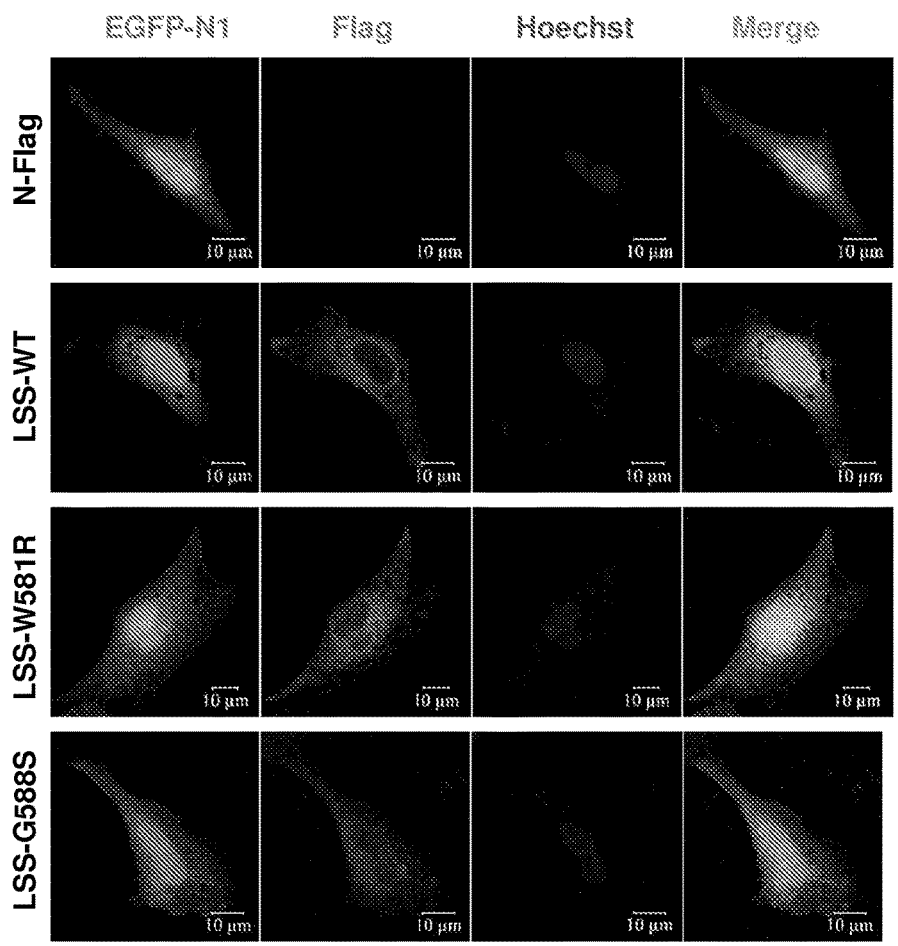
FIG. 7 shows representative confocal images of cells co-transfected with Flag-LSS and eGFP. Human lens progenitor cells were co-transfected with either the wild-type or the mutated LSS gene and the eGFP gene for 4 h and cultured for 16 h in fresh culture medium. The cellular distribution of LSS was then visualized using an anti-Flag antibody (purple). The distribution of eGFP (green) was used as a control. The nuclei were stained and visualized by Hoechst 33342 (blue).
Figure 8A:
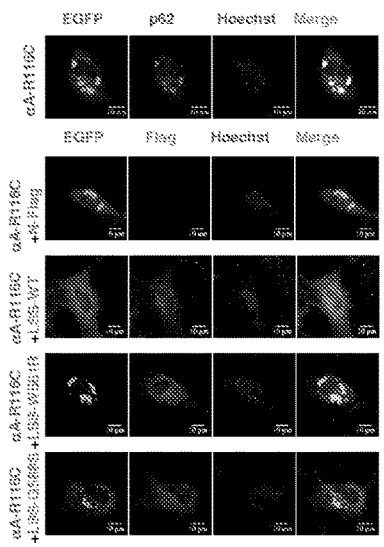
FIG. 8A, FIG. 8B, FIG. 8C, FIG. 8D, and FIG. 8E show representative confocal images of cells co-transfected with LSS and various cataract-causing crystallin mutants.
Figure 8B:
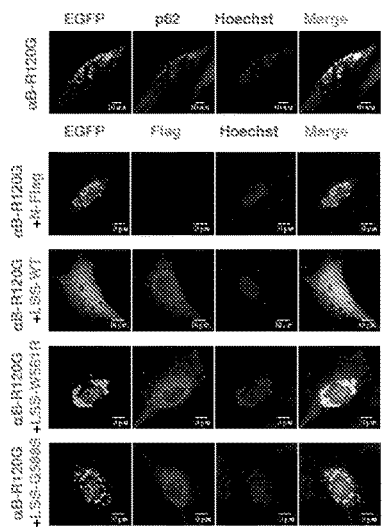
Figure 8C:
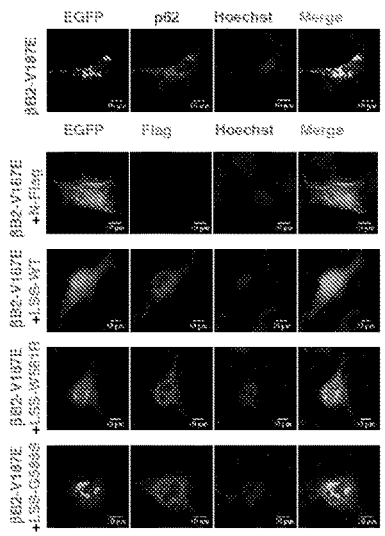
Figure 8D:
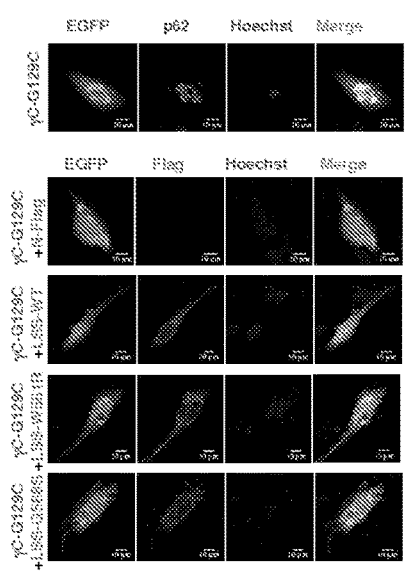
Figure 8E:
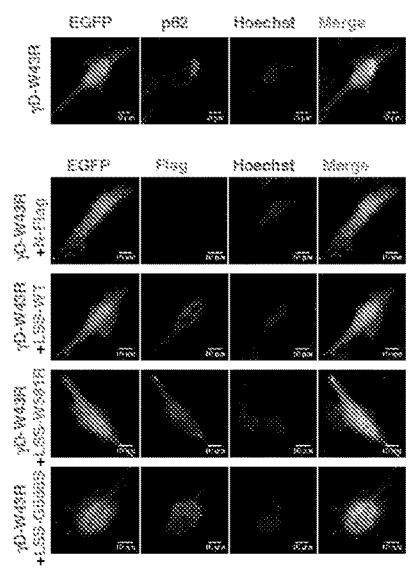
Figure 9A:
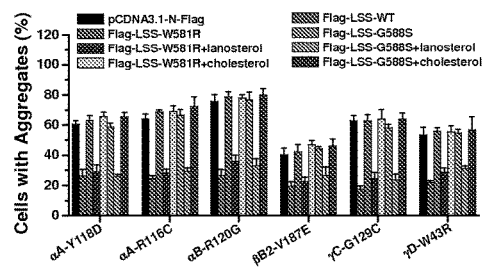
FIG. 9A, FIG. 9B, and FIG. 9C show inhibition of crystallin mutant aggregation by wild-type LSS and lanosterol in HLEB-3 cells (FIG. 9A) or HeLa cells (FIG. 9B). Cells co-transfected with LSS and crystallin mutant constructs were cultured for 24 h before assaying for aggregates. The rescue experiments were performed by addition of 40 € μM sterols (lanosterol or cholesterol) to the cell culture medium for 2 h, the sterol medium was then replaced with fresh culture medium and the cells were cultured for a further 12 h. The percentage of cells with crystallin aggregates were calculated from ten randomly selected viewing fields. The values of the wild-type LSS group, mutant group, or mutant plus lanosterol group were calculated. Aggregates were significantly lower in the wild-type LSS and lanosterol groups compared to the control group (P<1×10$^{-4}$), while aggregates in mutant LSS or cholesterol groups showed no difference to the control group (P>0.1).
Figure 9B:
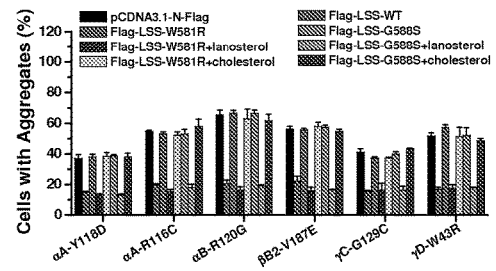
Figure 9C:
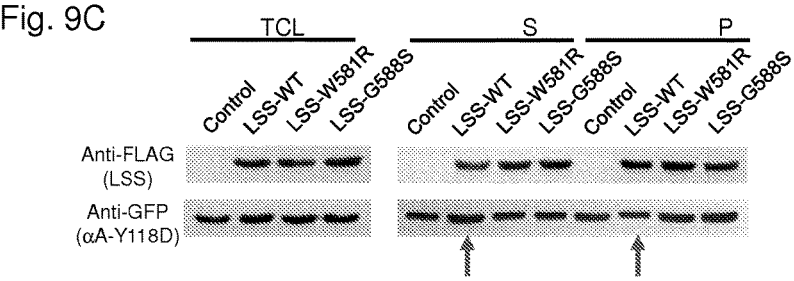
Figure 10A:
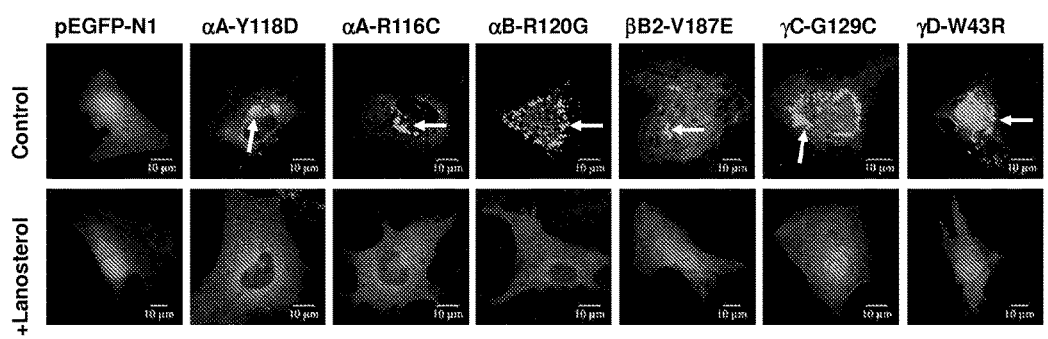
FIG. 10A, FIG. 10B, FIG. 10C, and FIG. 10D show lanosterol significantly reduced the intracellular aggregation caused by various cataract-causing mutant crystallin proteins in a concentration-dependent manner when assayed in HLEB-3 or HeLa cells.
Figure 10B:
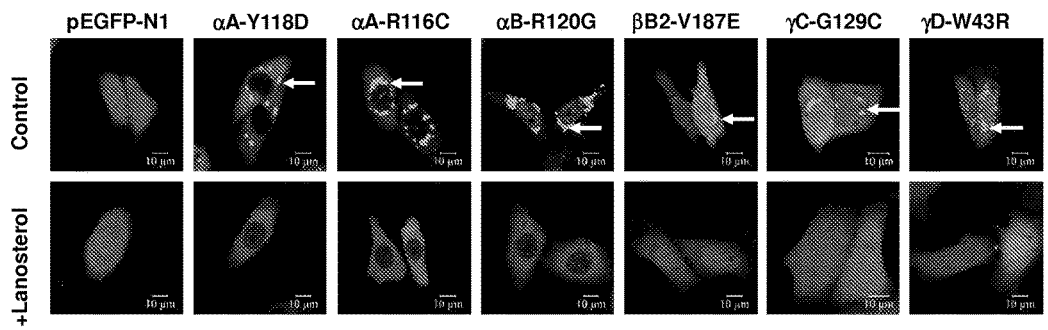
Figure 10C:
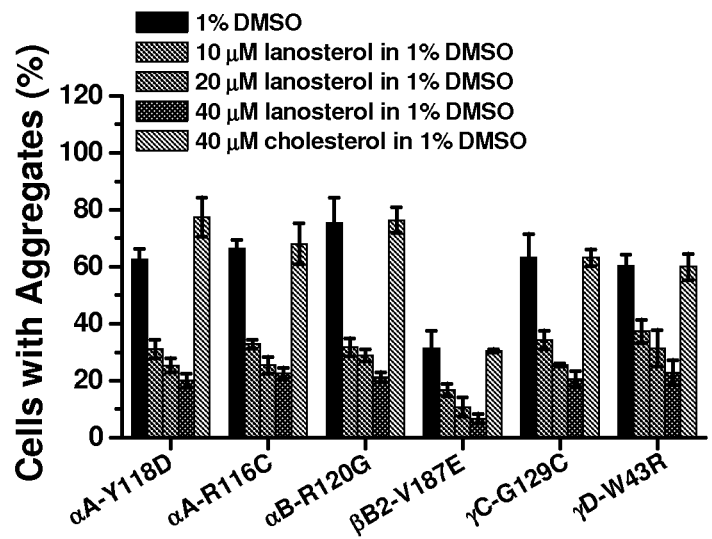
Figure 10D:
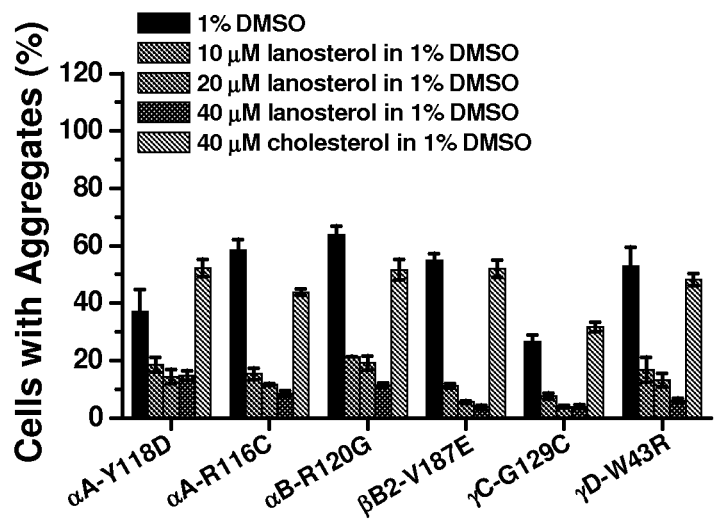

The amino acid residues W581 and G588 in LSS are highly conserved (FIG. 2A). We performed computational modelling analysis to investigate the effects of the W581R and G588S mutations on the 3D structure and function of LSS. The amino acid tryptophan at position 581 has been reported to contribute to the catalytic site of the cyclase activity[12]. The G588S mutant was modelled by in-place replacement followed by side-chain refinement. The S588 side-chain refinement could not resolve the van der Waals clash between the serine side chain and the backbone carbonyl of E578, which forms a key salt bridge with R639. The orientation of the E579:C584 loop needed to be distorted to accommodate the mutation. The side chain of the mutant S588 clashed into an adjacent loop, indicating that the mutation was incompatible with the normal enzymatic structure and function of LSS (FIG. 2B). Supporting the in silico results, expression of wild-type LSS in a cell transfection experiment exhibited cyclase activity and dramatically increased the amount of lanosterol production in the lipid fraction in HeLa cells, while neither the W581R nor the G588S mutant protein demonstrated any cyclase activity (FIG. 2C). In contrast, the cholesterol level was unaffected by the expression of wild-type or mutant LSS, suggesting that there may be an alternative pathway for cholesterol homeostasis. The W581R and G588S mutations did not alter subcellular localization or cause aggregates of LSS protein when compared to that of wild-type LSS, suggesting that the cataract phenotype was not due to the formation of light-scattering particles by mutant LSS proteins themselves (FIG. 7). The aggregation of crystallins, the major structural proteins in the lens, is a predominant cause of various types of cataracts[3]. To mimic protein aggregation in the cataractous lens, six known cataract-causing mutant crystallin proteins were expressed in human lens progenitor cells, human lens epithelial line B-3 (HLEB-3), or HeLa cells. These mutant crystallins formed p62-positive inclusion bodies/aggresomes in all three transfected cell lines, suggesting that aggregation is an intrinsic property of mutant crystallins (FIG. 3A and FIG. 8A-FIG. 8E, and FIG. 9A-FIG. 9C)[13]. Co-expression of wild-type LSS and a cataract-causing mutant crystallin protein significantly reduced both the number and size of intracellular crystallin aggregates, whereas LSS mutants failed to do so alone (FIG. 3B, C and FIG. 8A-FIG. 8E, and FIG. 9A-FIG. 9C). Western blot analysis indicated that the Y118Dmutant of αA-crystallin was released from intracellular aggregates and became more soluble with wild-type LSS (FIG. 3D and FIG. 9C). Furthermore, addition of lanosterol, but not cholesterol, in the culture medium of cells co-expressing an LSS mutant and a mutant crystallin successfully reduced crystallin aggregation (FIG. 3C and FIG. 8A-FIG. 8E, and FIG. 9A-FIG. 9C). This result indicated that lanosterol, but not cholesterol, could be an effective agent to release mutant crystallin proteins from aggregation.

Figure 3G:
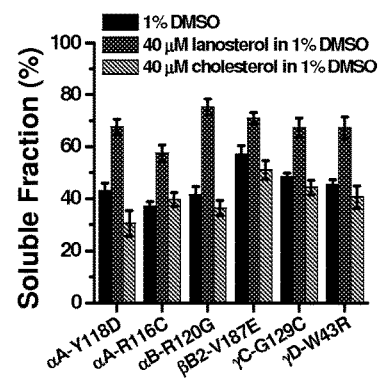
Figure 3H:
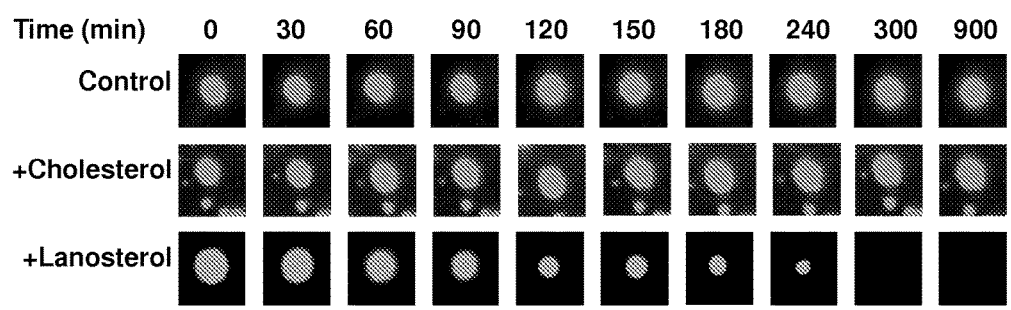
Figure 3I:
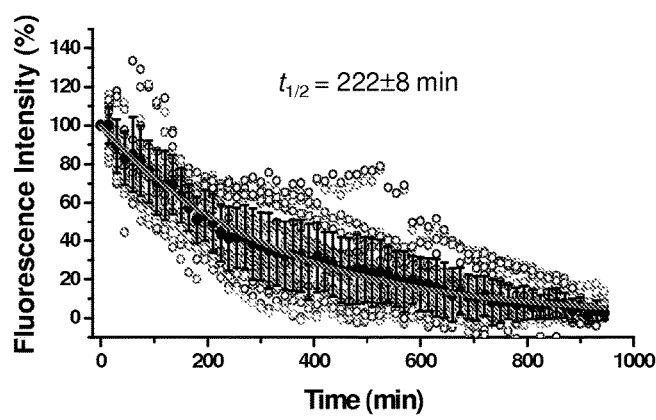
Figure 11A:
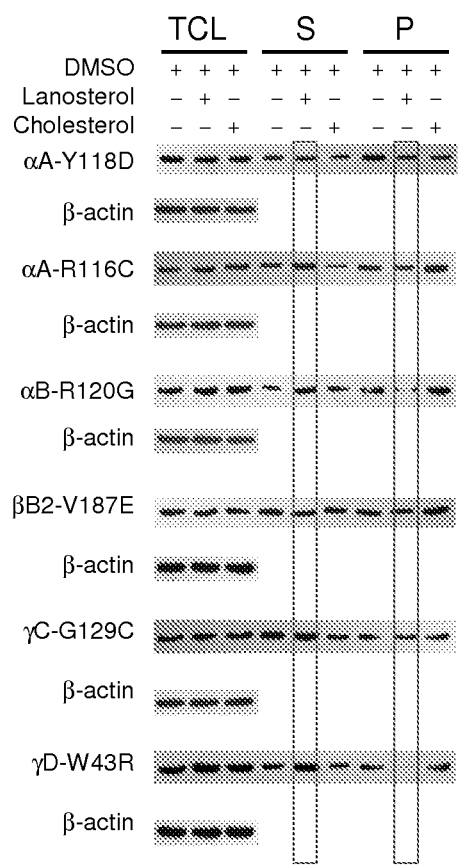
FIG. 11A, FIG. 11B, FIG. 11C, and FIG. 11D show treatment by lanosterol, but not cholesterol, increased cataract-causing mutant crystallins in soluble fractions when compared to a control group or a mutant LSS group.
Figure 11B:
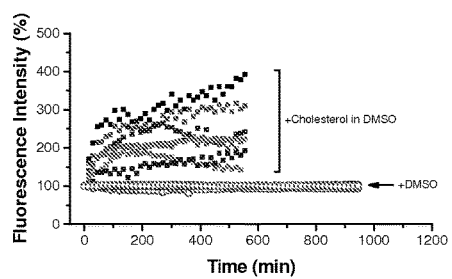

Supporting this hypothesis, lanosterol significantly inhibited aggresome formation of both wild-type and mutated crystallin proteins in a concentration-dependent manner, while cholesterol had no effect (FIG. 3E, FIG. 3F and FIG. 10A-FIG. 10D). Lanosterol, but not cholesterol, increased the amounts of mutant crystallins in the soluble fractions of cell lysates (FIG. 3G and FIG. 11A). Using serial live-cell imaging of cells expressing a GFP-fused Y118D mutant of aA-crystallin, we showed that addition of lanosterol could effectively diminish crystallin aggregates with a half-life of 22268 minutes (FIG. 3H), whereas addition of DMSO or cholesterol did not reduce aggresome formation (FIG. 11B). Single-particle tracking in live cells clearly showed that lanosterol has an important role in the dissociation of pre-formed intracellular protein aggregates.

Figure 4A:
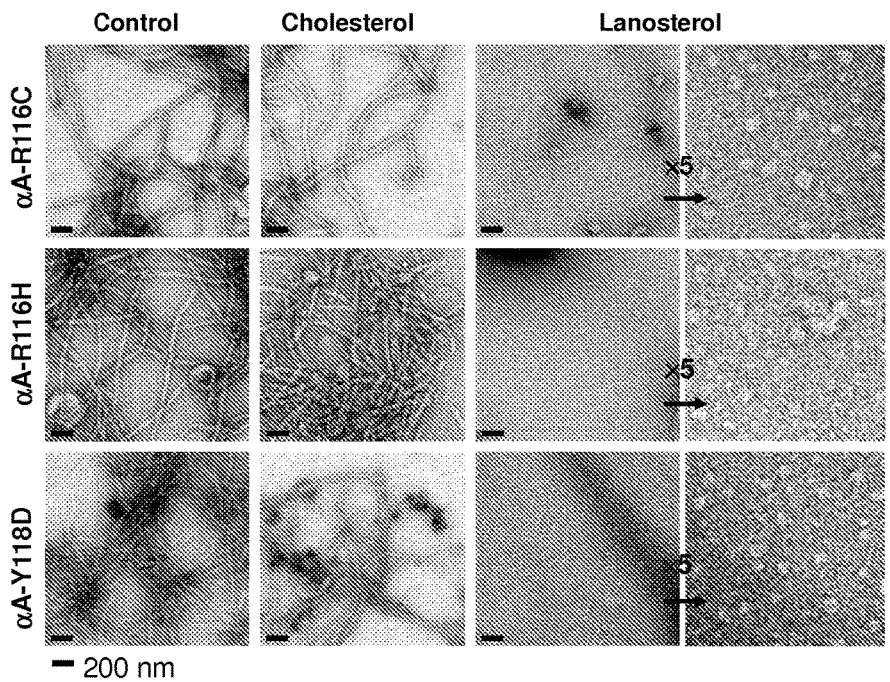
FIG. 4A and FIG. 4B show lanosterol re-dissolved preformed amyloid-like fibrils of crystallin proteins.
Figure 4B:
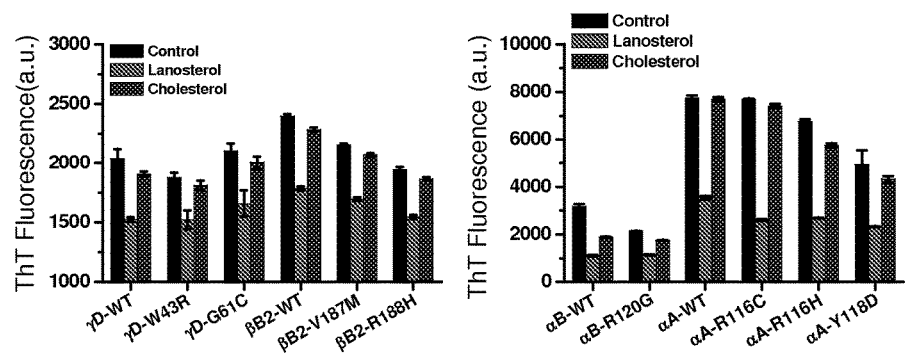
Figure 11C:
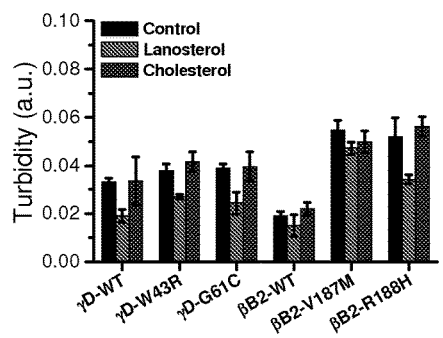
Figure 11D:
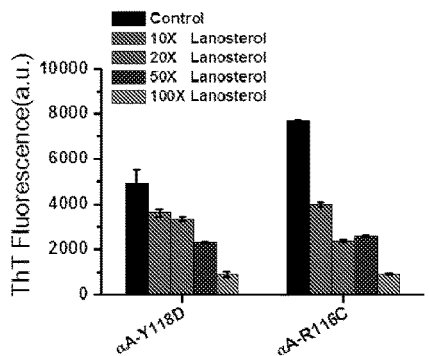
Figure 11D:
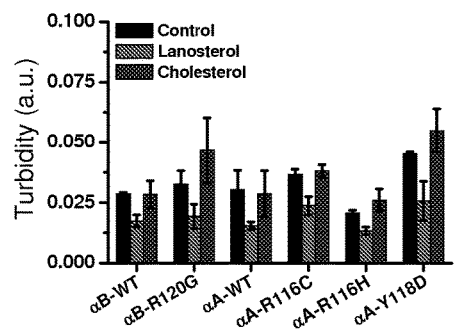

To investigate whether lanosterol has a direct effect on dissolution of the aggregated proteins, the aggregates of five wild-type and nine mutant crystallins were obtained by heating wild-type and mutated crystallins in the presence of 1M guanidine chloride. Under this condition, all crystallin proteins formed amyloid-like fibrils as revealed by the enhancement of thioflavin T (ThT) fluorescence, the fibrillary structures under negatively stained transmission electron microscopy (TEM), and the low turbidity value (FIG. 4A, FIG. 4B, and FIG. 11C). The morphology of the amyloid-like fibrils obtained here was similar to those crystallin proteins reported previously[14]. PBS containing liposomes formed by dipalmitoyl phosphatidylcholine (DPPC) was used to increase the solubility of sterol compounds and mimic the condition of sterols in cell membranes. Lanosterol, but not cholesterol, successfully re-dissolved the aggregated crystallin proteins from the amyloid-like fibrils in a concentration-dependent manner as indicated by the disappearance of fibrillar structures in the negatively stained TEM photographs and the decrease in ThT fluorescence intensity (FIG. 4A, FIG. 4B, and FIG. 11D). As an example, the re-dissolved αA-crystallins could be identified in negatively stained TEM pictures and were around 15 nm in size (FIG. 4A)[15].

Figure 5A:
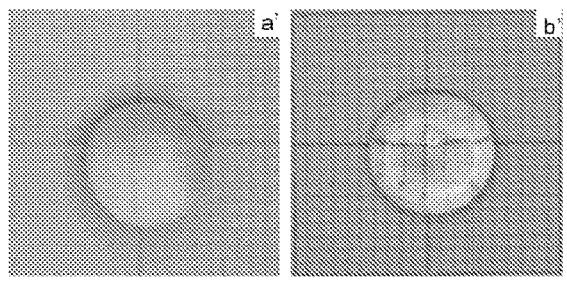
FIG. 5A, FIG. 5B, FIG. 5C, and FIG. 5D show lanosterol reduced cataract severity and increased clarity.
Figure 5B:
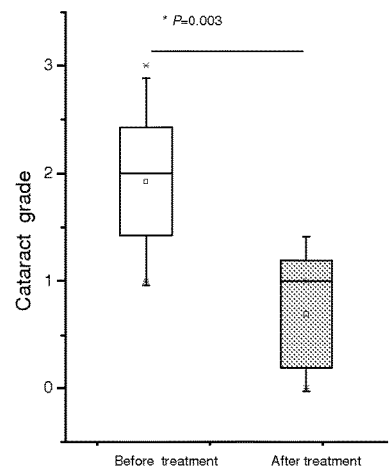
Figure 5C:
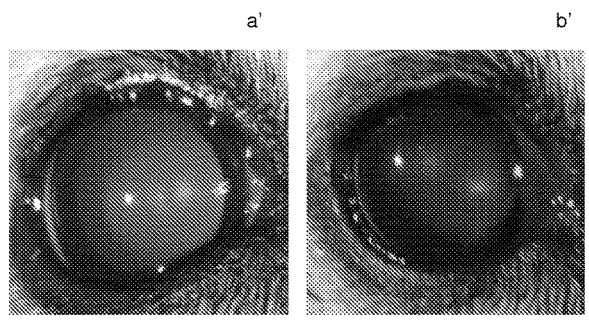
Figure 5D:
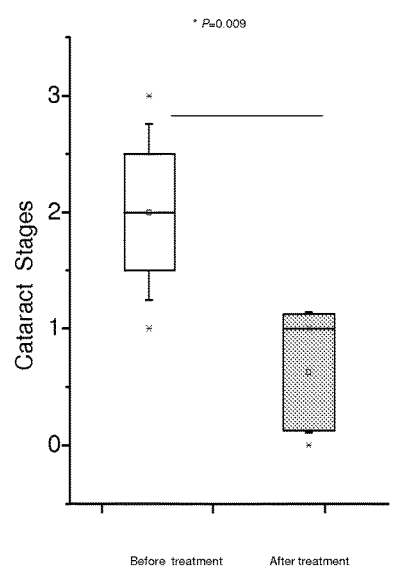
Figure 12A:
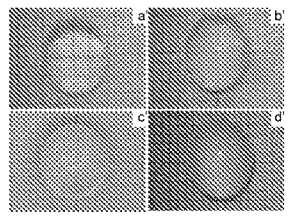
FIG. 12A, FIG. 12B, and FIG. 12C show grading system of cataractous lenses.
Figure 12B:
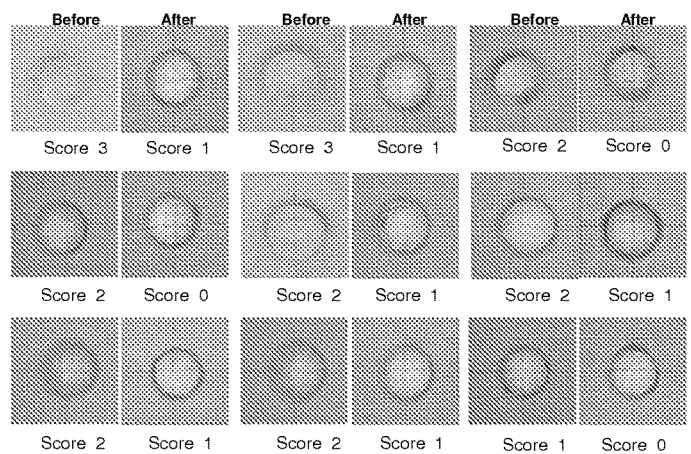
Figure 12C:
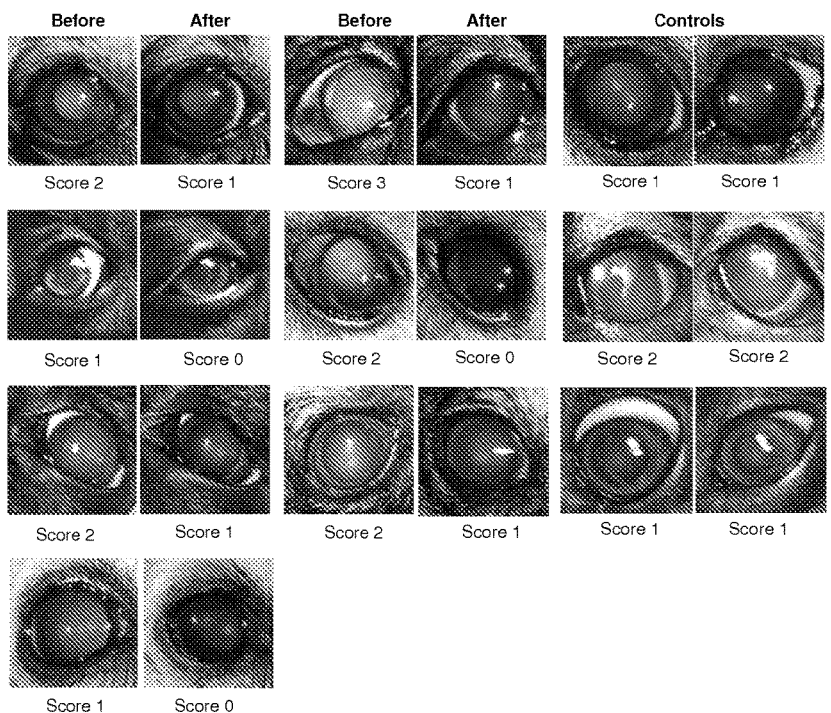

To assess the effect of lanosterol on cataract reduction in lens tissues, naturally occurring cataractous lenses from rabbits were isolated and incubated these in a 25 mM lanosterol solution for 6 days and compared lens clarity before and after treatment of lanosterol. A strong trend of reduction in cataract severity, as demonstrated by an increase in lens clarity (P<0.003, Wilcoxon Test, FIG. 5A, FIG. 5B, Table 2A and FIG. 12A, FIG. 12B) was observed. We further investigated the effect of lanosterol in reversing cataracts in dogs in vivo. Lanosterol treatment significantly reduced cataract severity and increased lens clarity (P<0.009, Wilcoxon Test, FIG. 5C, FIG. 5D; Table 2B and FIG. 12C).

Homozygous mutations affecting the catalytic function of LSS cause extensive congenital cataracts with severe vision loss. The critical role of lanosterol in cataract prevention is supported by the observation that a rat strain harbouring compound LSS mutations recapitulates the human cataract disease phenotype[6]. Consistent with this notion, inhibition of LSS by U18666A, an LSS inhibitor (also known as an oxidosqualene cyclase inhibitor), was found to cause cataracts[16]. Furthermore, lanosterol treatment markedly decreased protein aggregation caused by mutant crystallin proteins in cell culture, while reducing preformed cataract severity increasing lens clarity in animal models. It is conceivable that the amphipathic nature of lanosterol allows it to intercalate into and coat hydrophobic core areas of large protein aggregates, effectively allowing these aggregations to gradually become water soluble again.

In summary, lanosterol plays a key role in inhibiting lens protein aggregation and reducing cataract formation, suggesting a novel strategy for the prevention and treatment of cataracts. Cataracts are the leading cause of blindness and millions of patients every year undergo cataract surgery to remove the opacified lenses. The surgery, although very successful, is nonetheless associated with complications and morbidities. Therefore, pharmacological treatment to reverse cataracts could have large health and economic impacts. In addition, our results may have broader implications for the treatment of protein aggregation diseases, including neurodegenerative diseases and diabetes, which collectively are a significant cause of morbidity and mortality in the elderly population, by encouraging the investigation of mall-molecule approaches, such as the one demonstrated here.

Methods

Study participants. All participants had standard complete ophthalmic examinations and imaging studies. Demographic data, risk factors, and a blood sample were collected at the initial visit. We recruited a consanguineous family consisting of two adults and four children. The parents were first cousins, and three of their four children were diagnosed with retinal degeneration and cataract (FIG. 1A). We screened for LSS mutations in an additional 154 congenital cataract pedigrees and identified another family with a homozygous W581R mutation.

Exome capture and sequencing. Exome capture was carried out using Agilent SureSelect Human All Exon Kit (in solution) according to the manufacturer's protocols. Briefly, genomic DNA samples were randomly fragmented by Covaris with a base-pair peak of 150-200 bp for the resulting fragments, and adapters were ligated to both ends of the fragments. The adapter-ligated templates were purified using Agencourt AMPure SPRI beads, and fragments with insert size ~250 bp were excised. Extracted DNA was amplified by ligation-mediated PCR, purified, and hybridized to the SureSelect Biotinylated RNA Library (BAITS) for enrichment. Hybridized fragments bound to the strepavidin beads, whereas non-hybridized fragments were washed out after 24 h. Captured ligation-mediated PCR products were subjected to the Agilent 2100 Bioanalyzer to estimate the magnitude of enrichment. Each captured library was then loaded onto the Illumina Genome Analyzer II platform, and paired-end sequencing was performed with read lengths of 90 bp, which provided at least 50× average coverage depth for each sample. Raw image files were processed by Illumina base-calling software with default parameters.

Read mapping and variant detection. Sequence reads in each individual were aligned to the human reference genome (NCBI build 37, hg19) using BWA[17] (version 0.5.9-r16). BAM files created by BWA were then processed using the GATK[18] best practice pipeline using Genome Analysis Tool-Kit (version GATK 2.8) for re-alignment and variation (SNV and indel) detection. Variations that passed VQSR filtering criteria were extracted for the subsequent analyses.

The consensus genotypes in the target regions were called by SOAPsnp (v1.03) and BWA (version 0.5.9-r16) with the recommended parameters. A consensus genotype with Phred-like quality of at least 20 and at least 4× coverage depth was considered to be a high-confidence genotype. The genotypes that were different from the reference were extracted as candidate SNPs, and the SNP results were filtered as follows: Phred-like SNP quality >20, overall depth of 4× to 200×, copy number estimate <2, and distance between two adjacent SNPs no less than 5 bp.

Functional annotation of genetic variants. Variants were functionally annotated using ANNOVAR and categorized into missense, nonsense, read-through, and splice-site mutations, which are likely to be deleterious compared with synonymous and noncoding mutations. Based on these annotations, variants were filtered first for the nonsynonymous, splice acceptor-site and donor-site and then filtered against available public databases (dbSNP129 and 1000 Genome variants databases). The variants that were found to be homozygous mutations in the three affected subjects and heterozygous mutations in the carriers (parents), but were absent in the public databases, were considered to be candidate causal variants.

Mutation screening of LSS and gene. Sanger DNA sequencing was performed to validate the G588S mutation in LSS. The 22 exons of the LSS gene were amplified by PCR and sequenced on the Genetic Analyzer 3130 (Applied Biosystems). We screened for mutations in the LSS gene in 154 families with congenital cataracts and identified another homozygous mutation, W581R, in a second consanguineous family. These two mutations were absent in 11,000 control chromosomes, including 2,000 chromosomes from an unaffected control population in San Diego and the 1000 Genomes Project, and 8,000 chromosomes from an exome sequencing database at the University of Washington. Due to a previous report that a FDFT1 mutation modifies cataract phenotypes, we screened variants in the FDFT1 gene, identifying only one common non-synonymous variant rs4731 (GRch37/hg19: chr8:11666337; NM_001287742.1: c.134A.G,NM_001274671.1:p.K45R). The variant was excluded as the causal mutation since an unaffected daughter harboured the same homozygous change, and a relatively high frequency of general population possess this variant (minor allele frequency 0.4% in 1000 Genome Project data) (Table 1E).

3D modelling of the G588S mutation. The model of the G588S mutant was built from two structures as determined by Ruf et al.[20] and deposited in the Protein Data Bank as entries 1W6K and 1W6J[12]. The X-ray coordinates were used to build a full-atom model of the enzyme, and it was refined using the Internal Coordinate Mechanics program (ICM) and its PDB conversion protocol.[21] To analyse the effect of the G588S-mutation-induced clash on lanosterol binding, we analysed all side chains involved in the pocket of the enzyme interacting with lanosterol using the 1W6K structure. The areas of contact were calculated as the differences between the solvent-accessible area of each residue with and without lanosterol and were sorted by size using the ICM program.[22]

Plasmid constructs and site-directed mutagenesis. The clone containing LSS cDNA was purchased from Thermo Scientific Inc. The coding sequence of wild-type LSS was cloned and inserted into the pcDNA3.1-N-Flag plasmid (Invitrogen). The mutants were constructed via site-directed mutagenesis by overlap extension using PCR. The recombinant pcDNA3.1-N-Flag plasmids containing the wild-type or mutated LSS genes were transformed into E. coli DH5a cells. The cDNA of aA-, αB-, bB2-, cC- and cD-crystallin were cloned from the total cDNA of human lens as described previously.[23-26] The mutants were constructed by site-directed mutagenesis. The amplified fragments were digested by XhoI and BamHI, and then inserted into the eukaryotic expression vector peGFP-N1 or the prokaryotic expression vector pET28a. The plasmids were obtained using the Plasmid Maxiprep kit (Vigorous) and verified by DNA sequencing. Crystallin gene constructs were made as a C-terminus eGFP fusion protein, while LSS was made as an N-terminal Flag-tagged protein.

Cell culture and transfection. HeLa cells and human lens epithelial B-3 cells (HLEB-3) were obtained from ATCC. Human lens progenitor cells were isolated from a fetal human eye.[27] The HeLa cells were cultured in DMEM medium contain-ing 10% FBS (Gibco). The HLEB-3 cells were cultured in F12 medium with 20% FBS, while human lens progenitor cells were cultured in MEM medium containing 20% FBS and 10 mg ml$^{-1}$ FGF (Gibco). All cells were cultured at 37° C. in 5% $CO_2$ incubator. Cells routinely tested negative for mycoplasma contamination.

To assess the effect of LSS expression on sterol content, HeLa cells were trans-fected with wild-type LSS or LSS mutants fused with a Flag tag at the N-terminus of the coding region. The cells were harvested after 24 h transfection and the lipid fraction was extracted for LC-MS analysis. Cells transfected with the vector pcDNA3.1-N-Flag plasmids were used as a control. The expression levels of the wild-type and mutant LSS were normalized by western blot analysis using mouse anti-Flag (F1804; Sigma-Aldrich) and mouse anti-actin antibodies (B56007M; Bioworld Technology).

To assess the effect of lanosterol on crystallin aggregation, human lens progenitor cells were co-transfected with LSS and various crystallin constructs for 4 h. Cells co-transfected with crystallin mutants and pcDNA3.1-N-Flag were used as a control. Human lens progenitor cells co-transfected with LSS and crystallin mutant constructs were cultured for 12 h before assaying for aggregates. The rescue experiments were performed after 16 h by addition of 40 mM sterols (lanosterol or cholesterol, Sigma-Aldrich) to the cell culture medium for 2 h, which was then replaced with fresh culture medium and cells cultured for 24 h. The percentage of cells with crystallin aggregates was calculated from ten randomly selected viewing fields. The values of the wild-type LSS group, mutant group, and mutant plus lanosterol group were calculated. Cells treated with 1% DMSO were used as the controls.

The impact of LSS and lanosterol on intracellular crystallin aggregation were evaluated in single-blinded observer studies. Experiments have been repeated at least three times. P values were calculated using Student's t-tests. Fluorescence microscopy. Equal amounts of the human lens progenitor cells, HLEB-3 cells or HeLa cells were seeded on glass coverslips pretreated with TC (Solarbio). After culturing for 24 h to reach 90% confluency, the cells were transfected with plasmids containing various LSS or crystallin genes or co-transfected with plasmids containing a certain crystallin gene and those containing the wild-type or mutated LSS gene. The controls were cells transfected with the plasmids containing peGFP-N1 and/or peDNA3.1-N-Flag. Both transfection and co-transfection were performed using Lipofectamine 3000 (Invitrogen) according to the instructions from the manufacturer.

The effect of wild-type or mutated LSS on the intracellular aggregation of various cataract-causing crystallin mutants was evaluated by co-expression of Flag-LSS and crystalline-GFP in the human lens progenitor cells, HLEB-3 cells or HeLa cells. The intracellular distributions of the proteins were visualized using GFP or antibody against Flag. After co-transfection for 4 h, the cells were cultured in fresh media for 24 h, and then analysed by microscopy.

The effect of lanosterol or cholesterol on the aggresome formation of various crystallins was studied by transfecting the cells with plasmids containing various crystallin genes. The cells were incubated for 24 h to enable efficient protein expression and aggresome formation. The cells were then treated with 0-40 mM sterols in 1% (for human lens progenitor cells) or 2% DMSO (for HeLa cells). Cells treated with 1% or 2% DMSO were used as the control. After treatment for 2 h, the media was replaced with fresh media. After 12 h, the cells were used for microscopy analysis.

The microscopy samples were prepared by washing the slips with phosphate buffered saline (PBS) three times. The cells were fixed with 4% paraformaldehyde for 40 min followed by another three washes with PBS. The cells were permeabilized with 0.1% Triton X-100 (Sigma) in PBS for 10 min and blocked with 5% normal goat serum in PBS for 1 h at 37° C. Immunostaining was carried out by adding mouse anti-Flag antibody (1:500) or mouse anti-p62 antibody (1:200, ab56416; Abcam) in PBS buffer containing 5% normal goat serum and incubated for 1 h at 37° C. Then the slips were washed three times with PBS, and further incubated with Alexa 649-conjugated goat anti-mouse IgG (1:250) for 1 h at ambient temperature. The nuclei were counterstained with Hoechst 33342 (Invitrogen). The mounted cells were analysed using a Carl Zeiss LSM 710 confocal microscope.

Live-cell imaging. Human lens progenitor cells were transfected with plasmids containing αA-crystallin (Y118D) mutant. After a 24 h transfection period, the cells with stable expression of αA-crystallin (Y118D) mutant were screen by incubation in culture medium containing 0.8 mg ml$^{-1}$ G418 for 7 days. Then the obtained cells were seeded onto glass bottom cell culture dishes (In Vitro Scientific) and treated with 1% DMSO, 40 mM cholesterol in 1% DMSO or 40 mM lanosterol in 1% DMSO for 4 h. Fresh culture medium was added, and the cells were analysed by serial live-cell imaging. Live-cell images were viewed with an Olympus IX81 microscope and captured with CellSens Dimension software (Olympus). Quantitative analysis of the size of aggregates was performed by measuring the fluorescence intensity of p62-positive aggregates using single-par-tide tracking in live-cell imaging. The live-cell imaging was conducted using three biological replicates with 1-8 repetitions each.

Lipid extraction of the cells. Extraction of lipids was performed using the Bligh and Dyer method.[28] In brief, ~1×10$^6$-10$^7$ HeLa cells were washed 3-5 times with PBS and then scraped in 400-ml ice-cold methanol and transferred to a 1.5 ml Eppendorf tube with the addition of 200 ml chloroform. The samples were vortex-agitated for 1 min and then mixed with 300 ml of 1 M KCl. The organic and aqueous phases were separated by microcentrifugation at 20,817×g for 5 min at 4° C. After separation, the lower organic phase was collected. Then the residual aqueous phase was re-extracted twice using 300 ml chloroform. The collected organic phases were dried using a SpeedVac sample concentrator under vacuum. The dried samples were stored at 280° C. for further LC-MS analysis.

LC-MS analysis. The dried lipid extracts were re-suspended in 100 ml methanol. The samples were vortex-agitated for 10 min, treated by 80 W ultrasonic sonica-tion for 30 min, microcentrifuged at 20,817 g for 10 min, and then the supernatant was transferred to a new Eppendorf tube. The microcentrifugation treatment was repeated three times. The derived samples were analyzed by an Agilent 1290/6460 triple quadrupole LC/MS using an alternative Atmospheric Pressure Chemical Ionisation (APCI) source. The lipids were separated using an Agilent SB-C18 column. Selective ion monitoring was performed using the electron ionization mode. The highly pure lanosterol and cholesterol were used as controls. The MS determination was performed using a gas temperature of 350° C., a gas flow rate of 4 l min$^{-1}$, a nebulizer of 60 p.s.i., a vaporizer of 350° C., a capillary of 3,500 V and a corona current of 4 mA. To optimize the sensitivity and specificity, two qualifier ions were selected for the MS analysis of each compound (369.3/161.1 and 369.3/147 for cholesterol, and 409.2/191.3 and 409.2/109 for lanosterol). Western blotting. The cell lysates were prepared in RIPA buffer containing 50 mM Tris (pH 8.0), 150 mM NaCl, 1% Triton X-100, 1 mM EDTA, 0.5% sodium deoxycholate and 0.1% SDS. The supernatant and precipitation fractions were separated by centrifugation. The proteins were separated by a 12.5% SDS-PAGE and transferred to a PVDF membrane (GE Healthcare). The mouse anti-bodies against Flag (F1804; Sigma-Aldrich) or GFP (MB2005; Bioworld Technology) were used to identify the overexpressed LSS and crystallin proteins, respectively. Quantification of the western blot bands was achieved using the software GELPRO (Media Cybernetics). The presented quantitative data were calculated from three independent experiments.

Protein expression and purification. The recombinant His-tagged wild-type and mutated b- and c-crystallin proteins were overexpressed in *Escherichia coli* and purified using an Ni-NTA affinity column followed by gel filtration chromatography using the same protocol as described elsewhere[23,24,26,29]. The over-expression and purification of the non-tagged αA- and αB-crystallins were per-formed as described previously[30]. The purity of the proteins was estimated to be above 95% as evaluated by one homogeneous band on 12.5% SDS-PAGE, 10% native-PAGE and a single peak in the size-exclusion chromatography profile. The protein concentration was determined according to the Bradford method by using BSA as the standard[31]. All protein samples were prepared in 20 mM PBS buffer containing 150 mM NaCl, 1 mM EDTA and 1 mM DTT.

Protein aggregation and aggregate dissociation. The aggregates of the wild-type and mutated αA- and αB-crystallin proteins were obtained by heating the protein solutions containing 1 M guanidine chloride (ultrapure, Sigma-Aldrich) at a con-centration of 5 mg/ml at 60° C. for 2 h. The aggregates of the wild-type and mutated b- and c-crystallins were prepared by heating the protein solutions containing 1 M guanidine chloride at 37° C. for 48 h. The formation of aggregates was confirmed by ThT fluorescence, turbidity (absorbance at 400 nm) and transmission electron microscopy (TEM) observations. The preformed aggregates were re-suspended in 20 mM PBS with a final concentration of 0.2 mg/ml (approximately 10 mM). The re-suspended aggregates were treated with 500 mM lanosterol or cholesterol in liposomes formed by 500 mM DPPC (Sigma-Aldrich) at 37° C. Aggregates treated by 500 mM DPPC liposome were used as a negative control. After 24 h of treatment, the protein solutions were used for ThT fluorescence, turbidity and negatively stained TEM observations. The TEM samples were prepared by depositing the protein solutions onto a freshly glow-discharged carbon-coated copper grid. Negative-staining samples were obtained by staining the grid with 1.25% uranyl acetate for 30 s. The negatively stained TEM pictures were obtained on a Hitachi H-7650B transmission electron microscope with a voltage of 120 kV and a magnification of 48,000.

Treatment of cataractous rabbit lenses. Rabbits were euthanized by $CO_2$ inhalation and lenses were immediately dissected and treated with vehicle or lanosterol dissolved in vehicle to make 25 mM solutions. Lens tissues were incubated in these solutions for 6 days in the dark at room temperature. Cataracts were examined under a microscope and photographed. Degree of cataract was assessed by a blinded examiner using a previously described opacification grading system, shown below[32,33]. Improvements in lens clarity and transparency were quantified by visual inspection and grading. Lens clarity was scored by transmission of light, clarity of a grid image underneath the lens (FIG. 12A, FIG. 12B, FIG. 12C), and improvement in overall clarity of a lens or improvement in clarity of localized areas of cortical cataract. Wilcoxon test was used to evaluate the treatment effect.

Cataract grading system. Grade 0: absence of opacification (gridlines clearly visible); N Grade 1: a slight degree of opacification (minimal clouding of gridlines, with gridlines still visible); N Grade 2: presence of diffuse opacification involving almost the entire lens (moderate clouding of gridlines, with main gridlines visible); N Grade 3: presence of extensive, thick opacification involving the entire lens (total clouding of gridlines, with gridlines not seen at all)

Preparation of drug-loaded nanoparticles. Lanosterol was loaded into a lipid-polymer hybrid nanoparticle through an adapted nanoprecipitation method[34]. In brief, the desired concentration of lanosterol was mixed with polycaprolactone (PCL) polymer dissolved in acetonitrile. Lecithin and 1,2-distearoyl-sn-glycero-3-phosphoethanolamine-N-carboxy(polyethylene glycol) 2000 (DSPE-PEG-COOH) were dissolved in a 4% ethanol aqueous solution at 20% of the PCL polymer weight and heated above 60° C. The lanosterol/PCL solution was then added into the preheated lipid solution under gentle stirring followed by rigorous vortexing for 3 min. The mixture solution was then stirred for 2 h to allow the nanoparticles to form and the acetonitrile to evaporate. Next, the nanoparticle solution was washed three times using an Amicon Ultra-4 centrifugal filter (Millipore) with a molecular weight cut-off of 10 kDa to remove the remaining organic solvent and free molecules. The resulting nanoparticles were then re-suspended in PBS buffer for sub-sequent use. The size, size distribution, and surface zeta potential of the drug-loaded nanoparticles were characterized by dynamic light scattering. The loading yield of lanosterol was quantified by high-performance liquid chromatography.

Treatment of cataractous lenses in dogs. To assess the effect of lanosterol treatment on cataracts in live animals, dogs were pre-medicated with intramuscular injections of acepromaxine and butorphanol. After 20 min, induction of anaesthesia was performed by application of intravenous propofol. Dogs were then immediately intubated and maintained on oxygen and 2% isoflurane at 21 $min^{-1}$. Lanosterol (100 mg)-loaded nanoparticles were initially injected into the vitreous cavity in the test eye using a 28-gauge needle, and then were given every 3 days for the duration of the experiment. Treatment eyes or sham eyes were randomized. The control eye was given an injection with empty nanoparticle carriers as a negative control. The treatment eyes were treated with lanosterol in topical eye drops (see below for eye drop formulation). One 50-ml drop of lanosterol was administered three times daily to the test eye over 6 weeks. Degree of cataract severity was examined by slit lamp and photographed at the beginning and the end of the 6-week treatment period. Prior to examinations, pupils were dilated with 1% tropicamide and 10% phenylephrine. Degree of cataract severity was assessed by a blinded examiner and scored based on canine cataract stage, shown below[35]. Improvements in lens clarity and transparency were quantified. Wilcoxon test was used to evaluate the treatment effect.

Grading system of canine cataracts. Grade 0: absence of opacification (no cataract); N Grade 1: a slight degree of opacification (incipient stage); N Grade 2: presence of diffuse opacification involving almost the entire lens (immature stage); N Grade 3: presence of extensive, thick opacification involving the entire lens (mature stage) Topical vehicle solution. Double distilled $H_2O$ was added to 1.1 g $(EDTA)_2Na$ combined with 0.055 g alkyldimethylbenzylammonium chloride until a final volume of 1.1 l (pH 5.66) was achieved. 25 mM lanosterol in the topical vehicle solution. Double distilled $H_2O$ was added to a mixture of 12.5 g lanosterol, 1.1 g $(EDTA)_2Na$, 0.055 g alkyldimethylbenzylammonium chloride and 200 ml EtOH to a final volume of 1.11.

In one embodiment, a formulation of lanosterol eye drop solution is:
Recipe
A Vehicle Only Solution:

| | |
|---|---|
| Hydroxypropyl-β-Cyclodextrin | 165 g |
| Polysorbate 80 | 1 g |
| EDTA2Na | 1.1 g |
| Alkyldimethylbenzylammonium chloride | 0.055 g |
| EtOH | 200 ml |

Then add ddH2O till the final volume is 1.1 L (PH 5.66)

5 mM Lanosterol in a Vehicle Solution:

| | |
|---|---|
| Lanosterol | 2.5 g |
| Hydroxypropyl-β-Cyclodextrin | 165 g |
| Polysorbate 80 | 1 g |
| EDTA2Na | 1.1 g |
| Alkyldimethylbenzylammonium chloride | 0.055 g |
| EtOH | 200 ml |

Then add ddH2O till the final volume is 1.1 L (PH 5.66)

Table 1 Exome Sequencing and Variants

TABLE 1a

Summary of exome sequencing data production

| Sample | Total effective yield (Mb) | Average sequencing depth | Mismatch rate | Coverage of target region | Fraction of target covered >=4x | Fraction of target covered >=10x |
|---|---|---|---|---|---|---|
| IV-1 | 3,409.20 | 60.16 | 0.20% | 99.60% | 99.10% | 97.60% |
| IV-2 | 3,314.58 | 58.62 | 0.20% | 99.60% | 99.20% | 97.80% |
| IV-3 | 3,327.63 | 57.24 | 0.20% | 99.80% | 99.20% | 97.40% |
| III-2 | 3,029.40 | 51.89 | 0.21% | 99.80% | 99.30% | 97.70% |
| III-1 | 6,877.08 | 54.24 | 0.29% | 96.30% | 89.40% | 81.80% |
| IV-4 | 6,331.78 | 44.12 | 0.29% | 96.50% | 88.80% | 79.80% |

TABLE 1b

Summary of detected variants

| Sample | Total tion | Heterzygot | Homozygot | missense | nonsense | readthroug | synonymou | splicing | intergenic | intronic |
|---|---|---|---|---|---|---|---|---|---|---|
| IV-1 | 61,189 | 35,571 | 25,618 | 6,105 | 69 | 39 | 7,296 | 32 | 5,371 | 36,598 |
| IV-2 | 60,829 | 34,698 | 26,131 | 6,074 | 62 | 41 | 7,211 | 38 | 5,178 | 36,572 |
| IV-3 | 61,078 | 35,238 | 25,840 | 6,221 | 78 | 43 | 7,265 | 38 | 5,099 | 36,544 |
| III-2 | 62,753 | 39,001 | 23,752 | 6,393 | 64 | 38 | 7,588 | 34 | 5,764 | 36,924 |
| III-1 | 80,067 | 49,694 | 30,373 | 7,247 | 93 | 49 | 8,166 | 47 | 15,063 | 41,391 |
| IV-4 | 80,893 | 48,211 | 32,682 | 7,252 | 85 | 50 | 8,184 | 50 | 14,547 | 42,414 |

TABLE 1c

Variant prioritization pipeline after exome sequencing

| Filters | III-1 (carrier father) | III-2 (carrier mother) | IV-1 (affected daughter) | IV-2 (affected son) | IV-3 (affected son) | IV-4 (unaffected daughter) | Combine |
|---|---|---|---|---|---|---|---|
| Total variations | 80,067 | 62,753 | 61,189 | 60,829 | 61,078 | 80,893 | — |
| Missense, Nonsense, Splicing | 7,389 | 6,495 | 6,213 | 6,177 | 6,342 | 7,387 | — |
| Affected: 1/1; carrier: 0/1; unaffected: 0/1 or 0/0* | 5,792 | 4,661 | 3,127 | 3,123 | 3,085 | 5,638 | 9 |
| Not in dbSNP | 3,724 | 2,969 | 1,954 | 1,929 | 1,928 | 3,589 | 5 |
| Not in 1000 Genomes Project | 1,032 | 767 | 227 | 264 | 245 | 1,059 | 1 |
| Predicted damaging | 267 | 269 | 31 | 45 | 41 | 264 | 1 |

*Homozygous in affected child, heterozygous in carrier, no homozygous mutants in unaffected child

TABLE 1d

Summary of whole-gnome genotyping data

| Sample | Total loci | Captured | SNP |
|---|---|---|---|
| IV-1 | 4,641,218 | 4,440,318 | 559,832 |
| IV-2 | 4,641,218 | 4,446,992 | 605,499 |
| IV-3 | 4,641,218 | 4,445,267 | 526,794 |
| III-2 | 4,641,218 | 4,448,054 | 537,925 |
| III-1 | 4,641,218 | 4,446,581 | 574,880 |
| IV-4 | 4,641,218 | 4,450,657 | 584,347 |

Table 2 Treatment Effect of Lanosterol in Rabbit Cataract Lenses and Dog Cataract

TABLE 1e

Coding variants detected on gene FDFT1

| Position (GRch37/hg19) | refSNP | REF | ALT | Function | III-1 (carrier father) | III-2 (carrier mother) | IV-1 (affected daughter) | IV-2 (affected son) | IV-3 (affected son) | IV-4 (unaffected daughter) |
|---|---|---|---|---|---|---|---|---|---|---|
| chr8:11666337 | rs4731 | A | G | nonsynonymous | A/G | A/G | G/G | A/G | G/G | G/G |
| chr8:11683653 | rs904011 | T | C | synonymous | C/C | C/C | C/C | C/C | C/C | C/C |

TABLE 2a

Treatment effect of lanosterol in rabbit cataract lenses

| Sample number | Before treatment | After treatment |
|---|---|---|
| 1 | 3 | 1 |
| 2 | 2 | 0 |
| 3 | 2 | 1 |
| 4 | 2 | 0 |
| 5 | 3 | 1 |
| 6 | 2 | 1 |
| 7 | 2 | 1 |
| 8 | 2 | 0 |
| 9 | 1 | 1 |
| 10 | 1 | 0 |
| 11 | 2 | 1 |
| 12 | 1 | 1 |
| 13 | 2 | 1 |

TABLE 2b

Treatment effect of lanosterol in dog cataract

| Study eye | Treatment group | | Control group | |
|---|---|---|---|---|
| | Before | After | Before | After |
| 1 | 2 | 1 | 1 | 1 |
| 2 | 1 | 0 | 2 | 2 |
| 3 | 2 | 1 | 1 | 1 |
| 4 | 3 | 1 | | |
| 5 | 1 | 0 | | |
| 6 | 2 | 0 | | |
| 7 | 2 | 1 | | |

REFERENCES

1 Pascolini, D. & Mariotti, S. P. Global estimates of visual impairment: 2010. Br J Ophthalmol 96, 614-618, doi:10.1136/bjophthalmol-2011-300539 (2012).
2 Bloemendal, H. et al. Ageing and vision: structure, stability and function of lens crystallins. Prog. Biophys. Mol. Biol. 86, 407-485 (2004).
3 Moreau, K. L. & King, J. A. Protein misfolding and aggregation in cataract disease and prospects for prevention. Trends Mol Med 18, 273-282, doi:S1471-4914(12) 00039-1 [pii] 10.1016/j.molmed.2012.03.005 (2012).
4 Huff, M. W. & Telford, D. E. Lord of the rings—the mechanism for oxidosqualene:lanosterol cyclase becomes crystal clear. Trends Pharmacol Sci 26, 335-340, doi:S0165-6147(05)00127-6 [pii] 10.1016/j.tips.2005.05.004 (2005).
5 Diehn, J. J., Diehn, M., Marmor, M. F. & Brown, P. O. Differential gene expression in anatomical compartments of the human eye. Genome Biol 6, R74, doi:gb-2005-6-9-r74 [pii] 10.1186/gb-2005-6-9-r74 (2005).
6. Mori, M. et al. Lanosterol synthase mutations cause cholesterol deficiency-associated cataracts in the Shumiya cataract rat. J. Clin. Invest. 116, 395-404 (2006).
7 Ng, P. C. & Henikoff, S. Predicting deleterious amino acid substitutions. Genome Res 11, 863-874, doi:10.1101/gr.176601 (2001).
8. Adzhubei, I. A. et al. A method and server for predicting damaging missense mutations. Nature Methods 7, 248-249 (2010).
9. Pollard, K. S., Hubisz, M. J., Rosenbloom, K. R. & Siepel, A. Detection of nonneutral substitution rates on mammalian phylogenies. Genome Res. 20, 110-121 (2010).
10. Schwarz, J. M., Cooper, D. N., Schuelke, M. & Seelow, D. Mutation Taster2: mutation prediction for the deep-sequencing age. Nature Methods 11, 361-362 (2014).
11. Seelow, D., Schuelke, M., Hildebrandt, F. & Nurnberg, P. Homozygosity Mapper—an interactive approach to homozygosity mapping. Nucleic Acids Res. 37, W593-W599 (2009)
12 Thoma, R. et al. Insight into steroid scaffold formation from the structure of human oxidosqualene cyclase. Nature 432, 118-122, doi:10.1038/nature02993 (2004).
13. Dobson, C. M. Protein folding and misfolding. Nature 426, 884-890 (2003).
14. Ecroyd, H. & Carver, J. A. Crystallin proteins and amyloid fibrils. Cell. Mol. Life Sci. 66, 62-81 (2009).
15. Braun, N. et al. Multiple molecular architectures of the eye lens chaperone aBcrystallin elucidated by a triple hybrid approach. Proc. Natl Acad. Sci. USA 108, 20491-20496 (2011)
16 Cenedella, R. J. et al. Direct perturbation of lens membrane structure may contribute to cataracts caused by U18666A, an oxidosqualene cyclase inhibitor. J Lipid Res 45, 1232-1241, doi:10.1194/jlr.M300469-JLR200 M300469-JLR200 [pii] (2004).
17. Li, H. & Durbin, R. Fast and accurate long-read alignment with Burrows-Wheeler transform. Bioinformatics 26, 589-595 (2010).
18. DePristo, M. A. et al. A framework for variation discovery and genotyping using next-generation DNA sequencing data. Nature Genet. 43, 491-498 (2011).
19. Ruf, A. et al. The monotopic membrane protein human-oxido squalene cyclase is active as monomer. Biochem. Biophys. Res. Commun. 315, 247-254 (2004).
20. Cardozo, T., Totrov, M. & Abagyan, R. Homology modeling by the ICM method. Proteins 23, 403-414 (1995).
21. Abagyan, R. & Argos, P. Optimal protocol and trajectory visualization for conformational searches of peptides and proteins. J. Mol. Biol. 225, 519-532 (1992).
22. Xu, J. et al. The congenital cataract-linked A2V mutation impairs tetramer formation and promotes aggregation of bB2-crystallin. PLoS ONE 7, e51200 (2012).
23. Wang, B. et al. A novel CRYGD mutation (p. Trp43Arg) causing autosomal dominant congenital cataract in a Chinese family. Hum. Mutat. 32, E1939-E1947 (2011).
24. Gu, F. et al. A novel mutation in AlphaA-crystallin (CRYAA) caused autosomal dominant congenital cataract in a large Chinese family. Hum. Mutat. 29, 769 (2008).
25. Li, X.-Q. et al. A novel mutation impairing the tertiary structure and stability of cC-crystallin (CRYGC) leads to cataract formation in humans and zebrafish lens. Hum. Mutat. 33, 391-401 (2012).
26. Nagineni, C. N. & Bhat, S. P. Human fetal lens epithelial cells in culture: an invitro model for the study of crystallin expression and lens differentiation. Curr. Eye Res. 8, 285-291 (1989).
27. Bligh, E. G. & Dyer, W. J. A rapid method of total lipid extraction and purification. Can. J. Biochem. Physiol. 37, 911-917 (1959).
28. Wang, S., Leng, X.-Y. & Yan, Y.-B. The benefits of being b-crystallin heteromers: bB1-crystallin protects bA3-crystallin against aggregation during co-refolding. Biochemistry 50, 10451-10461 (2011).
29. Sun, T.-X., Das, B. K. & Liang, J. J. N. Conformational and functional differences between recombinant human lens aA- and aB-crystallin. J. Biol. Chem. 272, 6220-6225 (1997).

30. Bradford, M. M. A rapid and sensitive method for the quantitation of microgram quantities of protein utilizing the principle of protein-dye binding. Anal. Biochem. 72, 248-254 (1976).
31. Geraldine, P. et al. Prevention of selenite-induced cataractogenesis by acetyl-L-carnitine: an experimental study. Exp. Eye Res. 83, 1340-1349 (2006).
32. Makri, O. E., Ferlemi, A. V., Lamari, F. N. & Georgakopoulos, C. D. Saffron administration prevents selenite-induced cataractogenesis. Mol. Vis. 19, 1188-1197 (2013).
33. Zhang, L. et al. Self-assembled lipid-polymer hybrid nanoparticles: a robust drug delivery platform. ACS Nano 2, 1696-1702 (2008). La Croix, N. Cataracts: When to refer. Top. Companion Anim Med. 23, 46-50 (2008).
34. La Croix, N. Cataracts: When to refer. Top. Companion Anim Med. 23, 46-50 (2008).

What is claimed is:

1. A method to treat a vision disorder in a subject in need thereof, said method comprises administrating to at least one eye of the subject a composition comprising a pharmaceutically acceptable ophthalmic carrier and a pharmaceutically effective amount of lanosterol, wherein said composition is administered topically, subconjunctivally, retrobulbarly, periocularly, subretinally, suprachoroidally, or intraocularly, wherein said composition is formulated as an ophthalmic solution, an ophthalmic gel, an ophthalmic ointment, an ophthalmic wash, an intraocular infusion solution, a wash for anterior chamber, or preservative for extracted cornea; wherein said lanosterol dissolves crystallin protein aggregate in the at least one eye of said subject; and wherein said vision disorder is selected from the group consisting of cataract, congenital cataracts, cortical opacities, posterior subcapsular cataract, presbyopia nuclear sclerosis, retinal degenerative disorder, Refsum disease, Smith-Lemli-Opitz syndrome, Schnyder crystalline corneal dystrophy, drusen, age-related macular degeneration, and diabetic retinopathy.

2. The method of claim 1, wherein said subject is having or at risk of developing a vision disorder that affects the normal structure of the lens in the at least one eye.

3. The method of claim 1, wherein the vision disorder is cataract, and wherein said lanosterol dissolves lens crystallin protein aggregate in the at least one eye of said subject.

4. The method of claim 3, wherein the lens crystallin protein is selected from α-crystallin, β-crystallin, γ-crystallin, or combinations thereof.

5. The method of claim 1, wherein said subject is selected from the group consisting of amphibians, reptiles, avians, and mammals.

6. The method of claim 5, wherein said mammal is selected from the group consisting of rodents, cats, dogs, pigs, horses and humans.

7. The method of claim 1, wherein the lanosterol is administered in a sufficient amount and duration to dissolve amyloid-like fibrils of crystallin proteins.

8. The method of claim 7, wherein the method is done in situ, in vitro or in vivo.

9. The method of claim 7, wherein the crystallin protein is selected from α-crystallin, β-crystallin, γ-crystallin, or combinations thereof.

10. The method of claim 1, wherein the subject is human.

11. The method of claim 1, wherein the composition is administered topically.

12. The method of claim 1, wherein the vision disorder is cataract.

13. The method of claim 1, wherein the pharmaceutically acceptable carrier is selected from water, a buffer, or a solution of sodium chloride.

14. The method of claim 1, wherein the pharmaceutically acceptable carrier is a gel.

15. The method of claim 1, wherein the pharmaceutically acceptable carrier is an ointment.

16. The method of claim 1, wherein the pharmaceutically acceptable carrier is a cyclodextrin.

* * * * *